(12) United States Patent
Mazanec et al.

(10) Patent No.: US 8,029,748 B2
(45) Date of Patent: Oct. 4, 2011

(54) PROCESS AND APPARATUS FOR IMPROVED METHODS FOR MAKING VINYL ACETATE MONOMER (VAM)

(75) Inventors: Terry Mazanec, Solon, OH (US); Victor J. Johnston, Houston, TX (US); Michael Huckman, League City, TX (US); Sean P. Fitzgerald, Columbus, OH (US); James A. Foster, League City, TX (US); Daniel Lindley, Portland, TX (US); Anna Lee Tonkovich, Dublin, OH (US); Francis P. Daly, Delaware, OH (US); Leslie Wade, Pearland, TX (US); Tony Hammock, Bacliff, TX (US); Thomas Yuschak, Dublin, OH (US); Bin Yang, Columbus, OH (US); Kai Jarosch, Bexley, OH (US)

(73) Assignees: Velocys, Inc, Plain City, OH (US); Celanese International Corporation, Dallas, TX (US)

( * ) Notice: Subject to any disclaimer, the term of this patent is extended or adjusted under 35 U.S.C. 154(b) by 32 days.

(21) Appl. No.: 12/272,804

(22) Filed: Nov. 18, 2008

(65) Prior Publication Data
US 2009/0214404 A1 Aug. 27, 2009

Related U.S. Application Data

(63) Continuation of application No. 11/256,217, filed on Oct. 20, 2005, now Pat. No. 7,468,455.

(60) Provisional application No. 60/624,846, filed on Nov. 3, 2004.

(51) Int. Cl.
*B01J 8/04* (2006.01)
*B01J 19/30* (2006.01)
*B01J 19/18* (2006.01)
*B01J 19/00* (2006.01)
*B01J 8/02* (2006.01)
*B01J 35/02* (2006.01)
*B01J 8/00* (2006.01)
*C07C 67/00* (2006.01)

(52) U.S. Cl. ........ 422/630; 422/129; 422/130; 422/131; 422/198; 422/211; 422/631; 422/632; 422/633; 422/634; 422/635; 422/636; 422/637; 422/638; 422/639; 422/640; 422/603; 422/644; 422/647; 560/241

(58) Field of Classification Search .................. 422/188, 422/189, 190, 191, 193, 198, 129–131, 211, 422/600, 601, 630–640, 603, 644, 647; 560/241
See application file for complete search history.

(56) References Cited

U.S. PATENT DOCUMENTS
3,147,084 A * 9/1964 Franzen et al. ............... 422/652
(Continued)

FOREIGN PATENT DOCUMENTS
EP 0464633 A 1/1992

OTHER PUBLICATIONS
Office Action from Chinese Patent Application No. 200580037824.5, dispatched Sep. 4, 2009 (English translation).
(Continued)

*Primary Examiner* — Walter Griffin
*Assistant Examiner* — Natasha Young
(74) *Attorney, Agent, or Firm* — Frank Rosenberg

(57) ABSTRACT

The invention provides methods, apparatus and chemical systems for making vinyl acetate from ethylene, oxygen, and acetic acid.

16 Claims, 16 Drawing Sheets

U.S. PATENT DOCUMENTS

| | | | |
|---|---|---|---|
| 3,268,299 | A | 8/1966 | Russell |
| 3,518,284 | A | 6/1970 | Foster |
| 3,743,607 | A | 7/1973 | Russell |
| 4,739,124 | A | 4/1988 | Ward |
| 4,940,826 | A | 7/1990 | Font Freide et al. |
| 5,194,417 | A | 3/1993 | Smith et al. |
| 5,336,802 | A | 8/1994 | Smith et al. |
| 5,371,277 | A | 12/1994 | Matsumoto et al. |
| 5,550,281 | A | 8/1996 | Cirjak et al. |
| 5,731,457 | A | 3/1998 | Nicolau |
| 5,811,062 | A | 9/1998 | Wegeng et al. |
| 5,935,489 | A | 8/1999 | Hershkowitz et al. |
| 5,997,826 | A | 12/1999 | Lodeng et al. |
| 6,022,823 | A | 2/2000 | Augustine et al. |
| 6,117,578 | A | 9/2000 | Lesieur |
| 6,166,283 | A | 12/2000 | Bharadwaj |
| 6,190,624 | B1 | 2/2001 | Romantier |
| 6,274,113 | B1 | 8/2001 | Heyse et al. |
| 6,274,531 | B1 | 8/2001 | Nicolau |
| 6,315,977 | B1 | 11/2001 | Cantacuzene |
| 6,365,543 | B1 | 4/2002 | Schmidt et al. |
| 6,420,595 | B1 | 7/2002 | Hallinan et al. |
| 6,448,432 | B2 * | 9/2002 | Williams ..................... 560/245 |
| 6,488,838 | B1 | 12/2002 | Tonkovich et al. |
| 6,515,146 | B1 | 2/2003 | Perregaard et al. |
| 6,566,573 | B1 | 5/2003 | Bharadwaj |
| 6,616,909 | B1 * | 9/2003 | Tonkovich et al. ........ 423/648.1 |
| 6,620,965 | B1 | 9/2003 | Adams et al. |
| 6,680,044 | B1 | 1/2004 | Tonkovich et al. |
| 6,709,640 | B1 | 3/2004 | Romantier et al. |
| 6,756,340 | B2 | 6/2004 | Voskoboynikov et al. |
| 6,756,515 | B2 | 6/2004 | Rende et al. |
| 6,984,363 | B2 | 1/2006 | Tonkovich et al. |
| 7,294,734 | B2 | 11/2007 | Brophy et al. |
| 2003/0007904 | A1 | 1/2003 | Tonkovich et al. |
| 2003/0068261 | A1 * | 4/2003 | Taheri et al. ................... 422/197 |
| 2003/0180216 | A1 * | 9/2003 | TeGrotenhuis et al. ....... 423/659 |
| 2003/0187294 | A1 | 10/2003 | Hagemeyer et al. |
| 2004/0034266 | A1 | 2/2004 | Brophy et al. |
| 2004/0082804 | A1 | 4/2004 | Brophy et al. |
| 2005/0133457 | A1 | 6/2005 | Tonkovich et al. |
| 2005/0175519 | A1 | 8/2005 | Rogers et al. |
| 2009/0054683 | A1 | 2/2009 | Bueker et al. |

OTHER PUBLICATIONS

Office Action from Chinese Patent Application No. 200580037824.5, dispatched Jul. 1, 2010 (English translation).

International Search Report from PCT/US2005/039714.

* cited by examiner

PROCESS AND APPARATUS FOR IMPROVED METHODS FOR MAKING VINYL ACETATE MONOMER (VAM)

RELATED APPLICATIONS

This application is a divisional of U.S. patent application Ser. No. 11/256,217, filed Oct. 20, 2005, now U.S. Pat. No. 7,468,455. In accordance with 35 U.S.C. sect. 119 (e), this application claims priority to U.S. Provisional Application No. 60/624,846, filed Nov. 3, 2004.

FIELD OF THE INVENTION

This invention relates to apparatus and methods for making vinyl acetate from ethylene, oxygen, and acetic acid.

INTRODUCTION

Vinyl acetate ($CH_3COOCH=CH_2$), is otherwise known as vinyl acetate monomer (VAM), acetic acid ethenyl ester and acetic acid vinyl ester. Vinyl acetate is used mainly for the production of polymers and copolymers, e.g., for paints (mainly dispersions), adhesives, textile and paper processing, chewing gum, and for the production of poly(vinyl alcohol) and polyvinylbutyral. Vinyl acetate—ethylene copolymers are processed to give resins, paints, and sheeting. Floor coverings are made from vinyl acetate—vinyl chloride copolymers. Vinyl acetate is also used in small quantities as a comonomer in polyacrylic fiber production. Several means have been employed to produce vinyl acetate including the addition of acetic acid to acetylene in the gas phase over a solid catalyst and the reaction of acetic acid (ethanoic acid), ethylene (ethene) and oxygen:

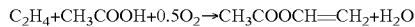

$$C_2H_4+CH_3COOH+0.5O_2 \rightarrow CH_3COOCH=CH_2+H_2O$$

The reaction takes place commercially in liquid phase using palladium/copper salts as homogeneous catalysts or in the gas phase over heterogeneous catalysts containing palladium. The reaction occurs at temperatures above 140° C. and at pressures of 0.5 to 50 atm. Byproducts are water, $CO_2$ and small quantities of ethyl acetate, ethylidene diacetate, and glycol acetates. The reaction is exothermic (−178 kJ/gm-mole).

Due to its economic importance, improvements have long been sought for the synthesis of vinyl acetate. In 1961, Russell described a process in which a mixture of acetylene and acetic acid were fed into a central distributor tube and out through holes spread along the length of a packed bed tube to form vinyl acetate (see Example 2 of U.S. Pat. No. 3,268,299). An advantage of this system is the avoidance of hot spots that can damage the catalyst. Russell mentioned that the holes along the length of the distributor tube could be replaced with alternate bands of a porous material.

During the 1960's, processes were developed for producing vinyl acetate monomer from the reaction of ethylene, oxygen, and acetic acid over a catalyst containing Pd, Au, and an alkalai metal acetate. See U.S. Pat. No. 3,743,607. More recently, various catalyst compositions have been for improvements of the synthesis of vinyl acetate monomer. For example, Augustine et al., in U.S. Pat. No. 6,022,823 describes processes of converting up to about 100% of oxygen, but at relatively low selectivity to VAM (high selectivity to $CO_2$). Similarly, Smith et al. in U.S. Pat. No. 5,194,417 reported high conversion but with high selectivity to carbon dioxide. Other workers, for example Cirjak in U.S. Pat. No. 5,550,281, have reported good selectivity, but at a high expense, namely, low conversion of ethylene (hence, the need for high recycle and expensive compression steps). Despite intense efforts over a long period of time, there remains a need for a process of making vinyl acetate monomer that is characterized by high conversion and low selectivity to carbon dioxide.

SUMMARY OF THE INVENTION

In a first aspect, the invention provides a method of making vinyl acetate, comprising: providing a reaction channel comprising a catalyst-containing reaction zone; and passing ethylene, acetic acid and dioxygen into the reaction channel. Inside the reaction channel, the ethylene, acetic acid and dioxygen react to form vinyl acetate monomer; where at least 20% of the ethylene is converted to products, and of the ethylene that is converted to products at least 80% is converted to vinyl acetate monomer or carbon dioxide. Also at least 60% of the dioxygen is converted to products; and at least 40% of the acetic acid is converted to products. The above-described conversions and selectivities are obtained in a single pass through the reaction channel. That the ethylene is "converted to products" means merely that the reactant is consumed, but does not require specified products, with the proviso that at least 80% (preferably at least 90%) of the ethylene is converted to vinyl acetate monomer or carbon dioxide. In a preferred embodiment, the above-described reaction channel comprises a single reaction zone.

In a second aspect, the invention provides a method of making vinyl acetate, comprising: providing a reaction channel comprising a catalyst-containing reaction zone; and passing ethylene, acetic acid and dioxygen into the reaction channel. In this method, the molar ratio of ethylene to dioxygen is 6:1 or less, and the concentration of dioxygen is at least 10% by mole. The ethylene, acetic acid and dioxygen react to form vinyl acetate monomer and carbon dioxide. At least 20% of the ethylene fed to the reaction channel is converted to products, and substantially all of the converted ethylene (i.e., the ethylene that is converted to products) is converted to vinyl acetate monomer or carbon dioxide. In this method, at least 20% of the oxygen is converted to products; and the selectivity of ethylene to carbon dioxide is 15% or less. The above-described conversions and selectivities are obtained in a single pass through the reaction channel. In a preferred embodiment, the above-described reaction channel comprises a single reaction zone.

In another aspect, the invention provides a method of making vinyl acetate, comprising: providing a reaction channel comprising a catalyst-containing reaction zone; and passing ethylene, acetic acid and dioxygen into the reaction channel. In the reaction channel the ethylene, acetic acid and dioxygen react to form vinyl acetate monomer. In this method, at least 20% of the ethylene is converted to products, and of the ethylene that is converted to products, at least 95% of the ethylene is converted to vinyl acetate monomer or carbon dioxide, with a selectivity to carbon dioxide is 10% or less. Also, at least 40% of the oxygen is converted to products. The above-described conversions and selectivities are obtained in a single pass through the reaction channel. In a preferred embodiment, the above-described reaction channel comprises a single reaction zone.

In a further aspect, the invention provides a process for the production of vinyl acetate monomer, comprising: passing ethylene, acetic acid, and dioxygen into a reaction channel, wherein the reaction channel comprises a reaction zone containing a catalyst; reacting the ethylene, acetic acid, and dioxygen over the catalyst to form VAM; wherein the partial pressure of acetic acid when calculated on the basis of the total feed to the reactor exceeds the dewpoint pressure of acetic acid at the reaction temperature.

In another aspect, the invention provides a process for the production of vinyl acetate monomer, comprising: passing ethylene, acetic acid, and dioxygen into a reaction channel, wherein the reaction channel comprises a reaction zone containing a catalyst; reacting the ethylene, acetic acid, and dioxygen over the catalyst to form VAM; wherein at least one of ethylene, acetic acid, and dioxygen are added in a staged fashion into at least two points along the length of the reaction channel.

In a further aspect, the invention provides apparatus for the production of VAM, comprising: a continuous reaction channel comprising at least 2 catalyst-free mixing zones alternating with at least 2 catalyst-containing reaction zones; and a cooling channel adjacent to the reaction channel.

An advantage of preferred embodiments of the invention is that vinyl acetate can be safely produced from relatively high concentrations of ethylene, acetic acid, and dioxygen with high selectivity and good yield. This makes possible a more economic process with substantially less recycle than conventional systems. The reaction can be done in microchannels, and can take advantage of the inherent safety of microchannels for mixtures of explosive reactants.

Particular features of the invention may be additionally illuminated by reference to previously submitted patent applications. An extensive discussion of manifolding in microchannel devices can be found in U.S. patent application Ser. No. 10/695,400 Descriptions of staging and mixing in microchannels can be found in U.S. patent application Ser. No. 10/848,559. A discussion of quenching and distributed feed in microchannels can be found in U.S. patent application Ser. No. 10/429,286. A description of apparatus suitable for scaled up production of VAM can be found in U.S. patent application Ser. No. 10/774,298, filed Feb. 6, 2004. All of these references are incorporated herein as if reproduced in full below. It is not believed that these references have conflicting terminology; however, if such conflicts are present, the terminology in the present description is controlling.

GLOSSARY

As is understood in the art, a "microchannel" is not merely an orifice. The length of a microchannel (that is, the direction of flow during normal operation) is not the shortest dimension of a microchannel. Both height and width of a microchannel are substantially perpendicular to the direction of flow of reactants through the reactor. Microchannels are also defined by the presence of at least one inlet that is distinct from at least one outlet—microchannels are not merely channels through zeolites or mesoporous materials. A microchannel has at least one dimension of 10 mm or less, preferably 5 mm or less, preferably about 2 mm or less, and more preferably 1 mm or less; and in some embodiments, 0.1 to 1 millimeters. Preferably, the length of a microchannel is greater than 1 cm, in some embodiments in the range of about 1 to 500 cm. The sides of the microchannel are defined by a microchannel wall or walls. The choice of material for the walls depends on the intended use. These walls are preferably made of a hard material such as a ceramic, an iron based alloy such as steel, or monel. In some embodiments, the microchannel walls are comprised of a stainless steel or Inconel® which is durable and has good thermal conductivity. The microchannel devices can be made by known methods, and in some preferred embodiments are made by laminating interleaved plates (also known as "shims"), and in some preferred embodiments, shims (either single or shim sets) designed for reaction channels are interleaved with shims (either single or shim sets) designed for heat exchange.

In some preferred embodiments, the microchannel devices are microchannel reactors that include a plurality of microchannel reaction channels, preferably in thermal contact with a plurality of adjacent heat exchange microchannels. A plurality of microchannels may contain, for example, 2, 10, 100, 1000 or more channels. In preferred embodiments, the microchannels are arranged in parallel arrays of planar microchannels, for example, at least 2 arrays of planar microchannels. In some preferred embodiments, multiple microchannel inlets are connected to a common header and/or multiple microchannel outlets are connected to a common footer. During operation, the heat exchange microchannels (if present) contain flowing heating and/or cooling fluids. Non-limiting examples of this type of known reactor usable in the present invention include those of the microcomponent sheet architecture variety (for example, a laminate with microchannels) exemplified in U.S. Pat. Nos. 6,200,536 and 6,219,973 (both of which are hereby incorporated by reference). Performance advantages in the use of this type of architecture include their relatively large heat and mass transfer rates, and the substantial absence of any explosive limits. Microchannel reactors can combine the benefits of good heat and mass transfer, excellent control of temperature, residence time, minimization of back diffusion, and minimization of by-product formation. Pressure drops can be low, allowing high throughput. Furthermore, use of microchannel reactors can achieve better temperature control, and maintain a relatively more isothermal profile, compared to conventional systems. In addition to the process microchannel(s), additional features such as microchannel or non-microchannel heat exchangers may be present. Microchannel heat exchangers are preferred. Heat exchange fluids may flow through adjacent heat transfer microchannels, and can be gases or liquids and may include steam, liquid metals, or any other known heat exchange fluids—the system can be optimized to have a phase change in the heat exchanger. In some preferred embodiments, multiple heat exchange layers are interleaved with multiple reaction microchannels (for example, at least 10 heat exchangers interleaved with at least 10 process microchannels). Microchannels are defined by microchannel walls that limit flow.

An "orifice" is a hole through a microchannel wall. Its length is usually the same as the thickness of the microchannel wall (unless it is slanted, or with an extruded or dimpled opening mouth, in which cases its length will be slightly different from this thickness). An "orifice" is not a T-joint or "Y" joint; in other words, a single channel formed by two channels that flow together (in the shape of a "T" or a "Y") is not an orifice. In general, the mixing lengths of a T or Y-joint are considerably longer than those created by orifices in the described invention. The lengths may be two times, five times, or even 10 times longer. The longer lengths create more time with a less well mixed feed stream; the results of more time with a lower mixing quality may be a lower selectivity to the desired product, a larger device, or increased safety concerns from a potentially flammable mixture.

"Opposing orifices" are orifices at opposite sides of a microchannel that may or may not be identical in size and geometry and are aligned such that molecules which flow through the opposing orifices collide with each other inside the microchannel. The opposing orifices may be aligned to intersect or may be offset.

A "reaction chamber" is a portion of a reactor that contains a solid catalyst.

A "reaction channel" is a volume defined by a channel wall or walls that comprise a reaction zone. The channel can be of any shape, and can have a cross-sectional shape such as a circle (i.e., the channel is a cylinder), square, rectangle, or octagon, and may include a combination of shapes such that the channel changes shape with length. A reaction channel is no limited as to size and may include conventionally sized tubes. In some preferred embodiments, the reaction channel is a microchannel.

A "reaction zone" is a portion of a channel in which, during reaction, a reaction occurs. In operation of a method of making vinyl acetate, a "reaction zone" is the volume of a process channel that contains catalyst and operates at a gas temperature at which there is a substantial rate of reaction, typically about 130° C. or greater. A reaction zone includes the area occupied by catalyst plus, in the case of a flow-by configuration, a bulk flow pathway by a catalyst. In some preferred embodiments, a reaction zone has a ratio of heat transfer surface area (the area of reaction zone wall or walls that contact a heat exchanger) to reaction zone volume of greater than 1.2 cm$^{-1}$; preferably greater than 2.0 cm$^{-1}$; in some embodiments 1.6 cm$^{-1}$ to 200 cm$^{-1}$; in some embodiments 1.8 cm$^{-1}$ to 50 cm$^{-1}$; and in some embodiments 2 cm$^{-1}$ to 30 cm$^{-1}$.

For purposes of the present invention, a "system" is a combination of apparatus and fluids in the apparatus. In some preferred embodiments, a system may further be described by properties such as pressure, temperature, flow rates and/or reactivity characteristics. Any of the apparatus described herein may also be described as a system that includes one or more fluids in the apparatus.

DETAILED DESCRIPTION OF PREFERRED EMBODIMENTS

I. Apparatus

Figure 1A:
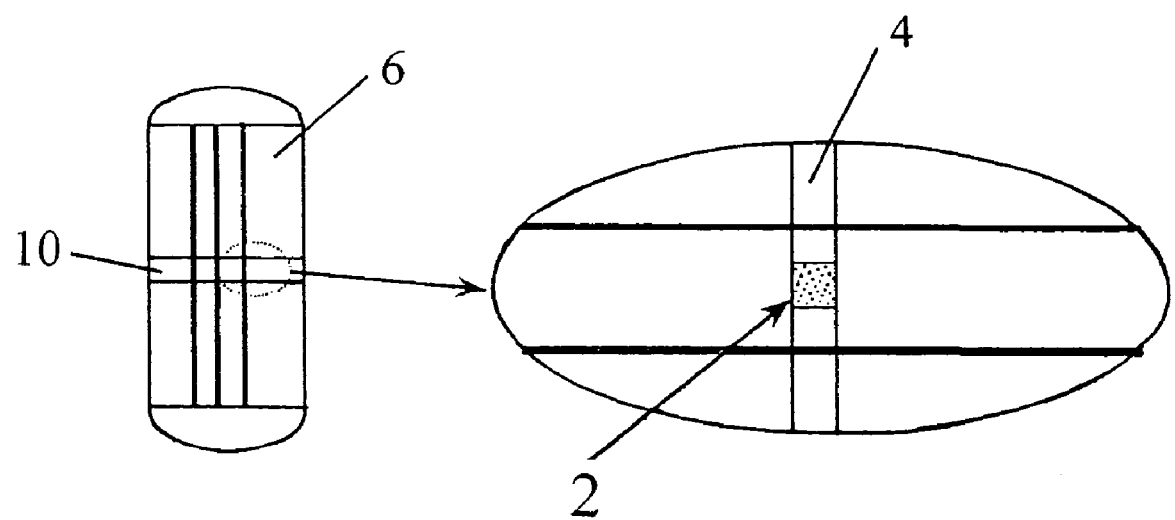
FIGS. 1A and 1B schematically illustrate tubular reactors having porous sections for staging a reactant.

The invention can provide increased capacity per unit by increasing the number of repeating units per reactor unit. A repeating unit comprises a reaction channel in thermal contact with a heat exchanger; and could be, for example, a layer of reaction channels in thermal contact with a layer of heat exchange channels. Repeating units can be stacked to increase capacity. In a shell and tube configuration, the repeating unit is a single tube. The number of repeating units connected together is preferably three or more, in some embodiments three to one thousand, and in some embodiments at least one hundred.

For controlling temperature of exothermic reactions, it is desirable for a heat exchanger (preferably one or more coolant channels, preferably coolant microchannels) to be disposed adjacent to a process channel. The process can be run in known apparatus, preferably microchannel apparatus such as apparatus in which layers of process channels (preferably at least 3) alternate with layers of coolant channels (preferably at least 4). For example, 3 alternating, interleaved layers would comprise layers in the order coolant:reaction:coolant: reaction:coolant:reaction. Typically, flow into and/or out of some or all of a plurality of coolant and/or endothermic reaction channels passes through a manifold or manifolds that combines or distributes the fluid flow. In preferred embodiments, microchannels are arranged in parallel arrays of planar microchannels; preferably a layer comprising a parallel array of planar microchannels is adjacent with another layer comprising a parallel array of planar microchannels where the adjacent layers exchange heat.

The height and/or width of a reaction channel (wall-to-wall, not counting catalyst) is preferably 17 mm or less, preferably 10 mm or less, preferably 5 mm or less, and more preferably 2 mm or less, and in some embodiments 50 to 1000 μm, and in some embodiments 0.05 to 2 mm. In some preferred embodiments, a reaction channel is regular or irregular in shape, and during operation, wherein one or more of such mass transfer, heat transfer and/or a chemical processing operation (or operations) occurs, at least in significant part, as fluid flows through fixed channels having surface-to-volume ratios of 10 or more square centimeters of channel internal surface area per cubic centimeter of channel internal volume; for the purposes of this definition, surface area and volume are determined on the basis of nominal internal channel dimensions, exclusive of surface area enhancers such as catalysts or catalyst supports in or on the walls of such channels. Height and width of a channel are perpendicular to the direction of flow. In some preferred embodiments, the portion of a reaction channel that contains a reaction zone or zones is less than 2 meters, more preferably less than 1 meter, and still more preferably less than 0.5 meter in length.

The catalyst can fill up a cross-section of a reaction (for VAM) and/or endothermic reaction channel (a flow-through catalyst) or only occupy a portion of the cross-section of a reaction channel (flow-by). The use of a flow-by catalyst configuration can create an advantageous capacity/pressure drop relationship. In a flow-by catalyst configuration, gas preferably flows in a 0.1-2.0 mm gap adjacent to a catalyst insert or a thin layer of catalyst that contacts a microchannel wall (preferably a microchannel wall that contacts the catalyst is in direct thermal contact with a coolant channel). The term "bulk flow path" refers to an open path (contiguous bulk flow region) within a reaction chamber. A contiguous bulk flow region allows rapid gas flow through a reaction chamber without large pressure drops. In preferred embodiments there is laminar flow in the bulk flow region. Bulk flow regions within each reaction channel preferably have a cross-sectional area of $5 \times 10^{-8}$ to $1 \times 10^{-2}$ m$^2$, more preferably $5 \times 10^{-7}$ to $1 \times 10^{-4}$ m$^2$. The bulk flow regions preferably comprise at least 5%, more preferably 30-80% of either 1) the internal volume of a reaction channel, or 2) a cross-section of a reaction channel.

In some embodiments, a static mixer is disposed at an inlet to a reaction channel.

Figure 1B:
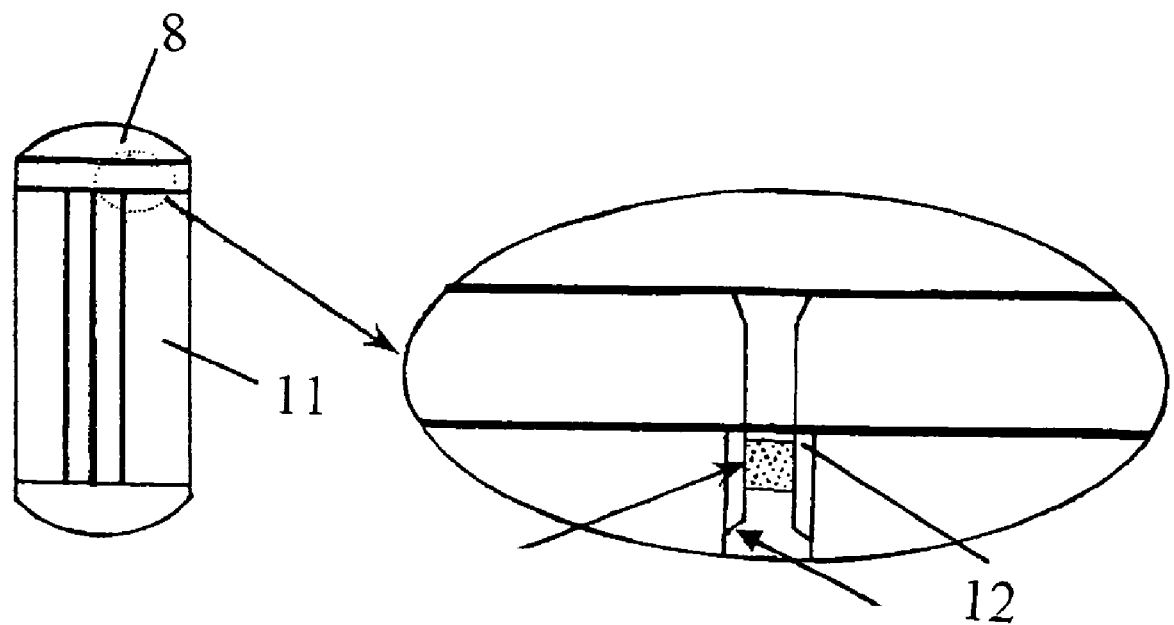

Staging can occur, for example, through orifices between adjacent channels. In one alternative embodiment, staged reactants can enter through porous sections disposed along the length of a process channel. FIGS. 1A and 1B schematically illustrate tubular reactors 6 and 8. The reactors can contain sealed sections 10, 11 that are pressurized with a reactant (such as O$_2$). The porous sections are preferably sections of sintered metal along the length of metal tubes 4. Although FIG. 1A illustrates only one pressurized, sealed section 10, there are preferably plural such sections, such as at least 2 or at least 10. FIG. 1B shows an embodiment with a porous section near the connection 12.

Microchannel apparatus can be made by known processes and can be made by processes such as stamping, partial etching, and spot welding features to backings. To make hermetic seals between layers in the reactor, diffusion bonding, braising and/or seam welding can be used.

Full scale reactors can be designed to be disassembled and repeating sub-assemblies can be separated from one another. The units may be gasketed together or seam welded. In the latter case, the perimeter weld would need to be removed to disassemble the unit. The use of repeating subassemblies is an advantageous design feature because it allows for the catalyst containing reactor sections to be refurbished as simple, discrete units without having to make special accommodations for the staging sub-assemblies. This feature also aids in the cleaning and maintenance of the entire full scale reactor. Multiple assemblies can be linked together in parallel to increase plant capacity. Sub-assemblies can use: orifice plates, foam, membrane material, etc. to redistribute product from a first subassembly that is then added to a second subassembly. Each of the subassemblies may be fabricated by the same or different methods.

Barrier Coatings and Material Protection

Vinyl acetate can be produced in stainless steel reactors, with or without barrier coatings to protect reaction channel walls. If barrier coating or coatings are used, they may be deposited by physical or chemical vapor deposition, or from solution or wash coating. In some embodiments, a barrier coating is selected from alumina, titania, silica, and combinations thereof. In one embodiment, material protection is provided by directly depositing a layer of alumina from a gas containing hydrogen, water, hydrogen chloride and aluminum trichloride. Wall coatings can protect reactor walls, but they can also be useful for adhering catalyst wall coatings.

Catalysts

The invention can employ any of the catalyst compositions known for the production of VAM. Suitable catalysts (and methods for making the catalysts) for catalyzing the production of VAM are well-known. Examples of catalysts for the production of VAM are described, for example, in U.S. Pats. Nos. 3,743,607, 3,775,342, 5,557,014, 5,990,344, 5,998,659, 6,022,823, 6,057,260, and 6,472,556; all of which are incorporated herein by reference. Preferred catalysts comprise Pd, Au, and, in some embodiments potassium acetate (KOAc). The catalysts also preferably contain a refractory support, preferably a metal oxide such as silica, silica-alumina, titania or zirconia, more preferably zirconia. The catalyst (preferably a catalyst layer) preferably comprises more than 2 weight % Pd, more preferably at least 4 wt % Pd; in some embodiments greater than 10 wt % Pd, and in some embodiments at least 12 wt % Pd. For thin layers or rim type catalysts, this weight percent refers to the entire layer or rim that contains a substantial amount of catalyst (i.e., catalyst that will have a significant impact on reactivity); it is not an arbitrarily selected portion of a thin layer or rim.

One process for making Pd/Au catalysts typically includes the steps of impregnating the support with aqueous solutions of water-soluble salts of palladium and gold; reacting the impregnated water-soluble salts with an appropriate alkaline compound e.g., sodium hydroxide, to precipitate (often called fixing) the metallic elements as water-insoluble compounds, e.g. the hydroxides; washing the fixed support material to remove un-fixed compounds and to otherwise cleanse the catalyst of any potential poisons, e.g. chloride; reducing the water insoluble compounds with a typical reductant such as hydrogen, ethylene or hydrazine, and adding an alkali metal compound such as potassium or sodium acetate. Various modifications to this basic process have been suggested. For example, in U.S. Pat. No. 5,990,344, Couves et al. suggested that sintering of the palladium be undertaken after the reduction to its free metal form. In U.S. Pat. No. 6,022,823, Augustine et al. suggested calcining the support in a non-reducing atmosphere after impregnation with both palladium and gold salts. In U.S. Pat. No. 5,466,652, Paparizos et al. suggested that salts of palladium and gold that are hydroxyl-, halide- and barium-free and soluble in acetic acid may be used to impregnate the support material. A similar suggestion is made in U.S. Pat. No. 4,902,823, i.e. use of halide- and sulfur-free salts and complexes of palladium soluble in unsubstituted carboxylic acids having two to ten carbons.

Preferred catalysts are of the rim or thin layer type in which the active metals are distributed in a thin rim or thin layer of material; thicker layers of active metals produce a higher proportion of undesirable side products. The rim or thin layer (or small particle) typically has a thickness of 50 to 1000 micrometers (μm), preferably 400 μm, more preferably in the range of 50 to 200 μm. For small catalyst particles having thicknesses less than these values, for example 1000 μm or less, active metals can be dispersed throughout the particles.

In some embodiments, the catalyst has a graded activity from one end of a reaction zone (or one end of a reaction channel) to the other end of the reaction zone (or other end of the reaction channel) such that the catalyst activity increases along the length of a zone or channel. In this fashion, the reaction can be moderated so that heat is generated more equally along the length of the zone or channel.

These compositions can take conventional forms such as powders and pellets, or can be deposited on a large pore support. Examples of suitable catalyst supports include felt (nonwoven fibers), foam, fin, screen mesh, gauze, honeycomb, or other porous structure. In some preferred embodiments, the catalyst is a catalytic wall coating (typically a washcoat) applied onto a channel wall or walls. The flow of reactants may be through the catalyst, as is typical in the case of a powder, foam, felt or gauze. The flow of reactants may also be around or 'by' a catalyst, such as by a wall coating, fin (i.e., catalyst coated on a fin or fins), or screen mesh disposed adjacent to a heat transfer wall (leaving a bulk flow path adjacent to the catalyst).

The highest number of catalyst sites per unit volume is envisioned for a powder catalyst or other flow-through structure such as a microporous packed bed of pellets or a foam. However, the corresponding pressure drop per unit length will also be highest for the flow through structures. At a contact time of 250 ms, the expected pressure drop per length for a powder catalyst ranges between 0.1 atm/m to 10 atm/m depending upon the size of particles, their shape, corresponding void volumes for flow and operating temperature and pressure of the reactor zone.

Figure 2A:
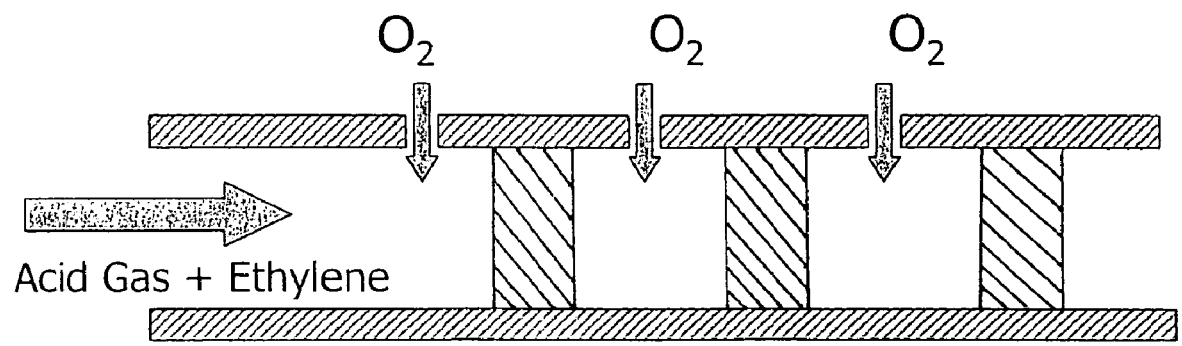
FIG. 2A schematically illustrates oxygen staging into a reaction channel.

In some preferred embodiments, a catalyst is intermittently disposed in a process channel for inter-stage mixing of reactants and/or liquid or gaseous catalyst life extenders, including air, oxygen, ethylene, acetic acid, or potassium acetate. In a preferred embodiment, orifices are disposed in between catalyst zones so that there is mixing but no, or substantially no, catalyzed reaction in regions between catalyst-containing zones. An example of this is schematically illustrated in FIG. 2A in which a catalyst 22 is disposed between mixing zones 24.

In some preferred embodiments, a reactor of the present invention comprises at least 10 cubic centimeters (cc), more preferably at least 20, and still more preferably at least 100 cc of solid catalyst (preferably in the form of a fixed bed). This amount of catalyst can be in a single channel but this much or more can be dispersed over plural reaction zones in plural reaction channels.

II. Process Control

Advantages possessed by the present invention include the ability to safely produce vinyl acetate in reactions that utilize high concentrations of reactants in near stoichiometric amounts. In some preferred embodiments, the process for the production of vinyl acetate has a ratio of ethylene to oxygen in the reactor of 6:1 or less throughout a reaction zone; more preferably 4:1 or less throughout a reaction zone; and still more preferably 2.5:1 or less throughout a reaction zone. In some preferred embodiments, the process for the production of vinyl acetate has a ratio of acetic acid to oxygen of 6:1 or less throughout a reaction zone; more preferably a ratio of 4:1 or less throughout a reaction zone; and more preferably a ratio of 2.5:1 or less throughout a reaction zone. In some preferred embodiments, the relative amounts of reactants are in the range of ethylene:acetic acid:dioxygen of 6:3:1 and 2:2:1. In some preferred, the $O_2$ concentration in a reaction channel is at least 8%, in some embodiments at least 16%, and in some embodiments in the range of 9 to 20% (by mol).

An advantage of the invention is lower need for recycling as compared to conventional processes. In a preferred embodiment of a steady-state reaction, the ratio of gaseous recycle to fresh feed is less than 10:1, more preferably 6:1 or less, still more preferably 2:1 or less, more preferably 1:1 or less, and most preferably 0.5:1 or less.

In preferred embodiments, a reactant is staged through plural (preferably at least 3) openings into a reaction channel. See, for example, FIG. 2A. Any combination of ethylene, oxygen or acetic acid can be staged into the process channel. For example, acetic acid or a mixture of acetic acid and oxygen can be added through plural orifices along the length of a process channel containing a catalyst and flowing ethylene.

Figure 2B:
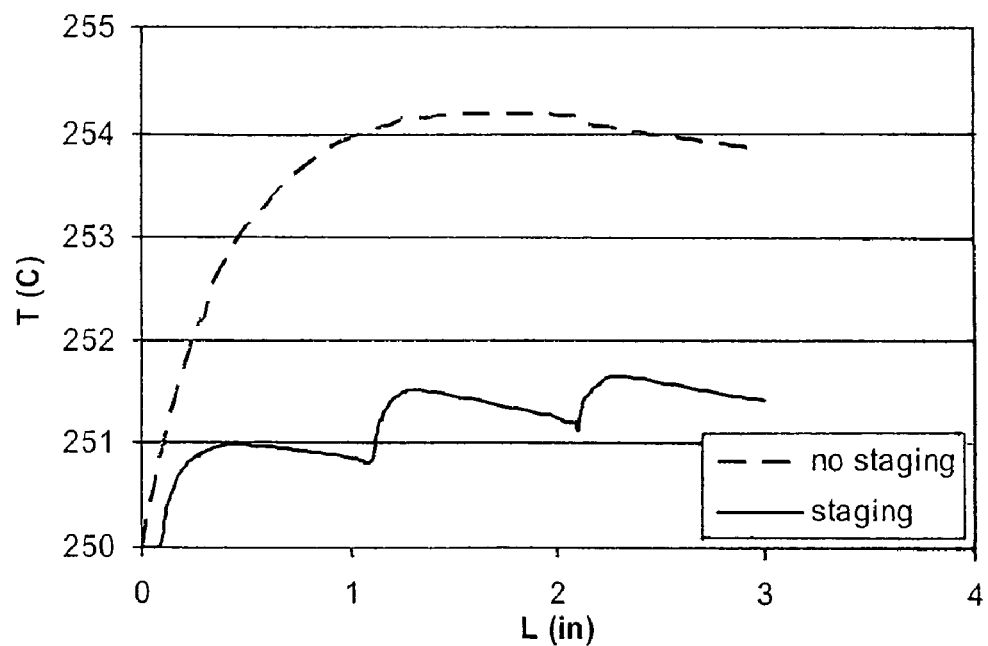
FIG. 2B shows a plot comparing a reaction for producing VAM with (solid line) and without (dashed line) staged addition of a reactant.

Staging of a reactant or reactants can provide improved temperature control. Tight temperature range in reactors helps maintain high product selectivity and increase the catalyst lifespan. For the case of no staging, all reactants are premixed and fed into the inlet of the reactor. The maximum temperature is observed at a certain location which is determined by the reaction rate and the heat transfer feature of the catalyst bed as exemplified by the dashed curve in FIG. 2B. The solid curve is the temperature profile for an equal bed size, overall feed rate and temperature but with three distinct feed locations within the reactor bed. Staging can reduce the temperature rise within a reactor as compared to the temperature rise for a pre-mixed feed.

Staging also provides another means of controlling the rates of reactions in the reactor zone. Thus, without staging, the concentration of the reactants is at a maximum at the reactor inlet. Due to the high concentration of feeds, the reaction rates are increased. This depletes the reactants, such that the concentrations of feed components decrease rapidly and the reaction rate is slowed. The overall reaction rate is the average of the incremental rates throughout the reaction zone, but the majority of the reaction occurs early on in the zone. By staging the feeds, the reaction rates can be moderated at the inlet and increased further down the reaction zone. This allows more effective use of all of the catalyst, while avoiding having excessive reaction occur over any particular portion of the reaction zone.

In some preferred embodiments, staging occurs by injecting one or more reactants through plural openings in a continuous process channel. Optionally, reactants may alternatively, or additionally, be added into manifold regions (headers or footers) that connect plural channels. In some preferred embodiments, the mixing areas adjacent the injection points (orifices) do not contain catalyst. Thus, in some preferred embodiments, a continuous process channel has catalyst-free mixing zones alternating with catalyst-containing reaction zones (such as at least 2 mixing zones alternating with at least 2 reaction zones). In this case, a "continuous" channel is a channel that does not flow into a manifold and back into the channel.

Figure 3:
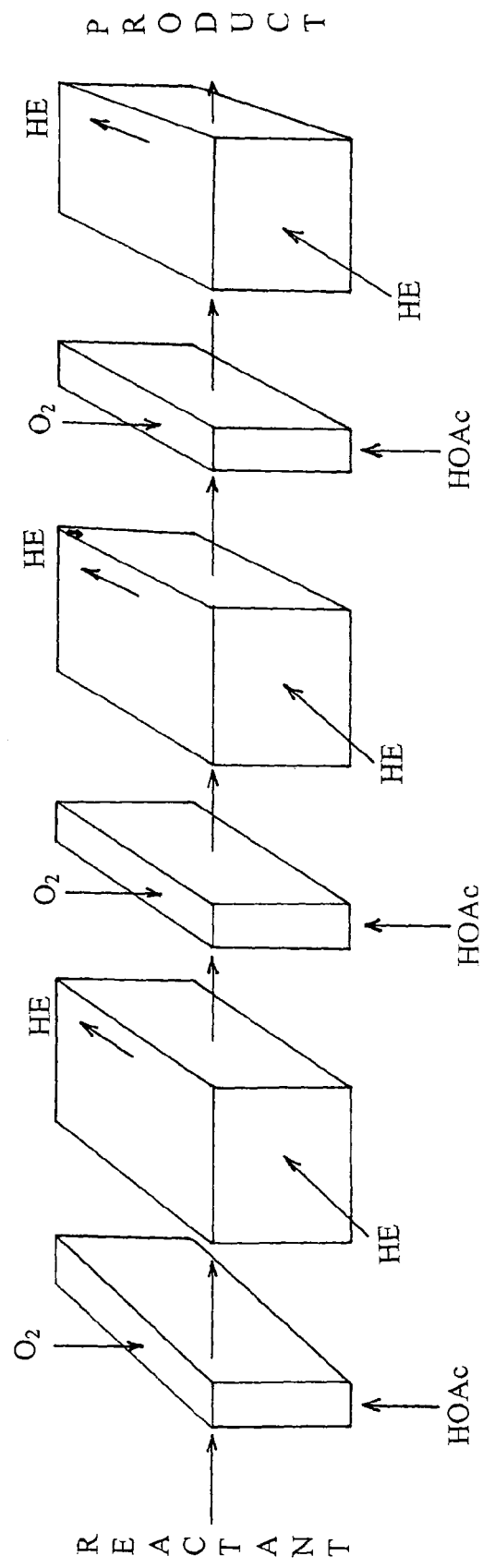
FIG. 3 schematically illustrates a staged addition reactor formed by joining subassemblies. The reactor subassembly (HE) contains catalyst and heat exchange channels.

A preferred configuration for making vinyl acetate is schematically illustrated in FIG. 3. This configuration includes two repeated sub-assemblies. The first such sub-assembly can be described as the reactor section and thus has housed within it all of the catalyst needed to perform the VAM reaction. The second sub-assembly can be described as the staging section and thus has oxygen and/or other streams injected/mixed into the main reactant stream. This configuration allows for these sub-assemblies to be alternated such that a full scale reactor is constructed consisting of multiple reactor sub-assemblies separated by staging sub-assemblies. This allows for oxygen and/or other streams to be mixed into the main reactant stream immediately prior to and/or immediately following the catalyst sections of the reactor. The reactor section sub-assembly can be greatly simplified due to the absence of mixing geometry and allows for the inclusion of heat exchange channels that can be located on both sides of any/all of the reactant channels. Likewise, the staging section sub-assembly can be simplified due to the absence of any catalyst channels and can therefore be designed to allow for multiple streams to be simultaneously mixed. FIG. 3 shows two such streams (O2 & acetic acid) being mixed into the reactant stream in stages and it should be understood that many different streams can be mixed together with the reactant stream in a similar configuration.

The reaction kinetics and reaction heat can be considered to determine the number of feed points and locations. The flow rate through each of opening is controlled by the size and shape of the orifice. Mixing efficiency can also be considered in selecting the orifice shape. For the case of catalyst packed-beds, near the injection points, no packing is preferred because of the detrimental effect of exposing the unmixed reactants to the catalyst. In some preferred embodiments, the length of the empty channel section near each injection point is at least about 8 times the hydraulic diameter of the channel—preferably, approximately the characteristic mixing length in micro-channels. Since the gap size is small in micro-channels, the total mixing length is a modest value compared to the overall channel length dimensions.

While oxygen is shown as the distributed species in FIG. 2A, it is possible to stage acetic acid with or without oxygen. This option would allow for production of vinyl acetate by the oxidation of a mixture of ethylene and acetic acid in which the partial pressure of acetic acid when calculated on the basis of the total feed to the reactor exceeds the dew point pressure of acetic acid at the reaction temperature (as measured at the inlet of the reaction zone; or, alternatively, the peak temperature within the process channel). By distributing throughout the bed, the acetic acid partial pressure can be kept high to push the reaction rate forward while keeping its partial pressure low enough to avoid condensation in the reactor. As acetic acid is consumed, distribution points keep the partial pressure high. The presence of liquid acetic acid would be deleterious to the results and could destroy the activity of the catalyst. In preferred embodiments of the invention in which acetic acid is added via staged addition to a process channel, the acetic acid is converted as it goes, and more is fed such that the total fed exceeds that corresponding to the dew point pressure; however, the acetic acid does not actually condense in the reaction zone because the partial pressure of acetic acid remains below the dew point at all points along the reaction channel. Although staged addition is preferred; it is believed that a process channel could operate without staging, but instead having a flow of liquid acetic acid into a reaction zone that is separated from the catalyst, preferably by a vapor permeable membrane.

In preferred methods, any and all of the reactants have short contact times in the reaction zone. Preferably 1 to 750 ms, in some embodiments 10 to 500 ms, in some embodiments 150 to 500 ms, and in some embodiments 100 to 400 ms. For example, ethylene can have a contact time of 500 ms or less in a reaction zone or zones; or oxygen can have a contact time of 500 ms or less, or a mixture of ethylene and acetic acid have a contact time of 500 ms or less in a reaction zone, etc. The contact times are much less than in conventional reactors. The speed of the reaction can also be described in terms of linear velocity and/or space velocity.

In some preferred embodiments, linear velocity (or mass flow rate) of the gas through the reaction zone is greater at the outlet of the reaction zone than it is at the inlet to the reaction zone (e.g., because some oxygen is added to the feed in a staged manner along the reactor length).

In some embodiments, the feed streams consist only of acetic acid, ethylene and dioxygen. In some embodiments, other components may also be present, for example, diluents such as nitrogen, water vapor, and carbon dioxide. In some embodiments, other gases that are essentially inert to the reaction conditions may also be employed. In some embodiments, the oxygen-containing stream contains less than 90% $O_2$. In some embodiments, air is used as the oxygen supply.

Total pressure (which can be defined either at the inlet, the outlet or both, or averaged throughout a reaction channel) is, in some embodiments, in the range of 1 to 20 bar, in some embodiments in the range of 5 to 15 bar.

Temperature in reaction zone is preferably at least 130° C., in some embodiments in the range of 120 to 400° C., in some embodiments 140-200° C., and in some embodiments 150-180° C. In preferred embodiments, temperature (measured by thermocouples at (or in) the reaction channel walls) over at least 50% of the length of a reaction channel (or at least 50% of the length of a reaction zone) varies by less than 10° C., more preferably 5° C. or less; this is in contrast with conventional reactors that typically have hot spots that are 10° C. to 15° C. higher than the average temperature of the catalyst bed. In preferred embodiments, temperature over at least 50% of the length of a cooling channel (adjacent to a reaction channel) varies by less than 10° C., more preferably 5° C. or less.

Figure 4:
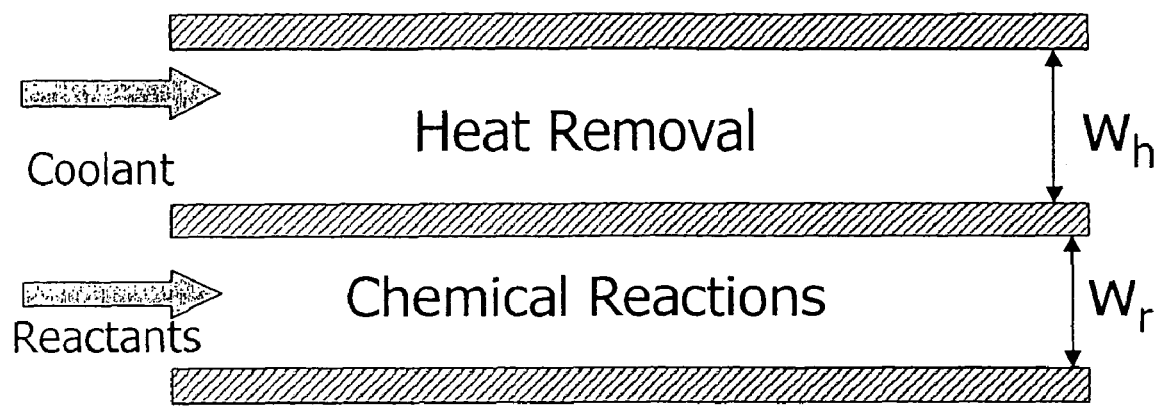
FIG. 4 schematically illustrates a section of a microchannel matrix repeating unit, with co-current coolant and process reaction flow.

It is desirable to control temperature rise in the reactor. The temperature rise inside the reactor for VAM production has a detrimental effect on the desired product selectivity and reduces catalyst life. In preferred embodiments, heat is removed through adjacent heat exchanger microchannels. The microchannel reactor configuration has a substantial volumetric productivity advantage over a bulky conventional shell and tube reactor. FIG. 4 schematically illustrates a section of a microchannel matrix repeating unit, with co-current coolant and process reaction flow.

Figure 5A:
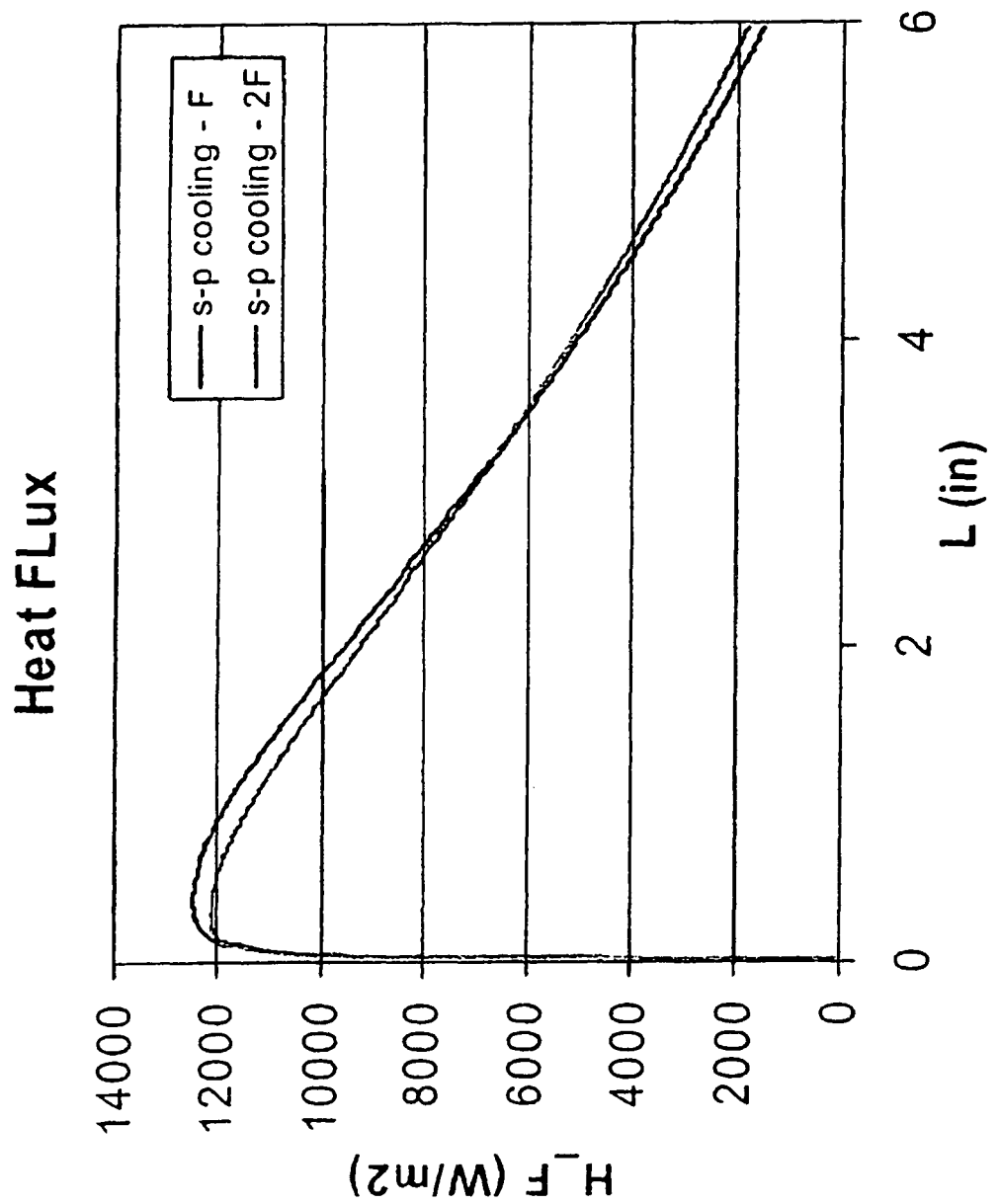
FIG. 5a shows heat flux and FIG. 5b shows temperature as a function of distance for single phase convective heat transfer in a microchannel configuration without staging.
Figure 5B:
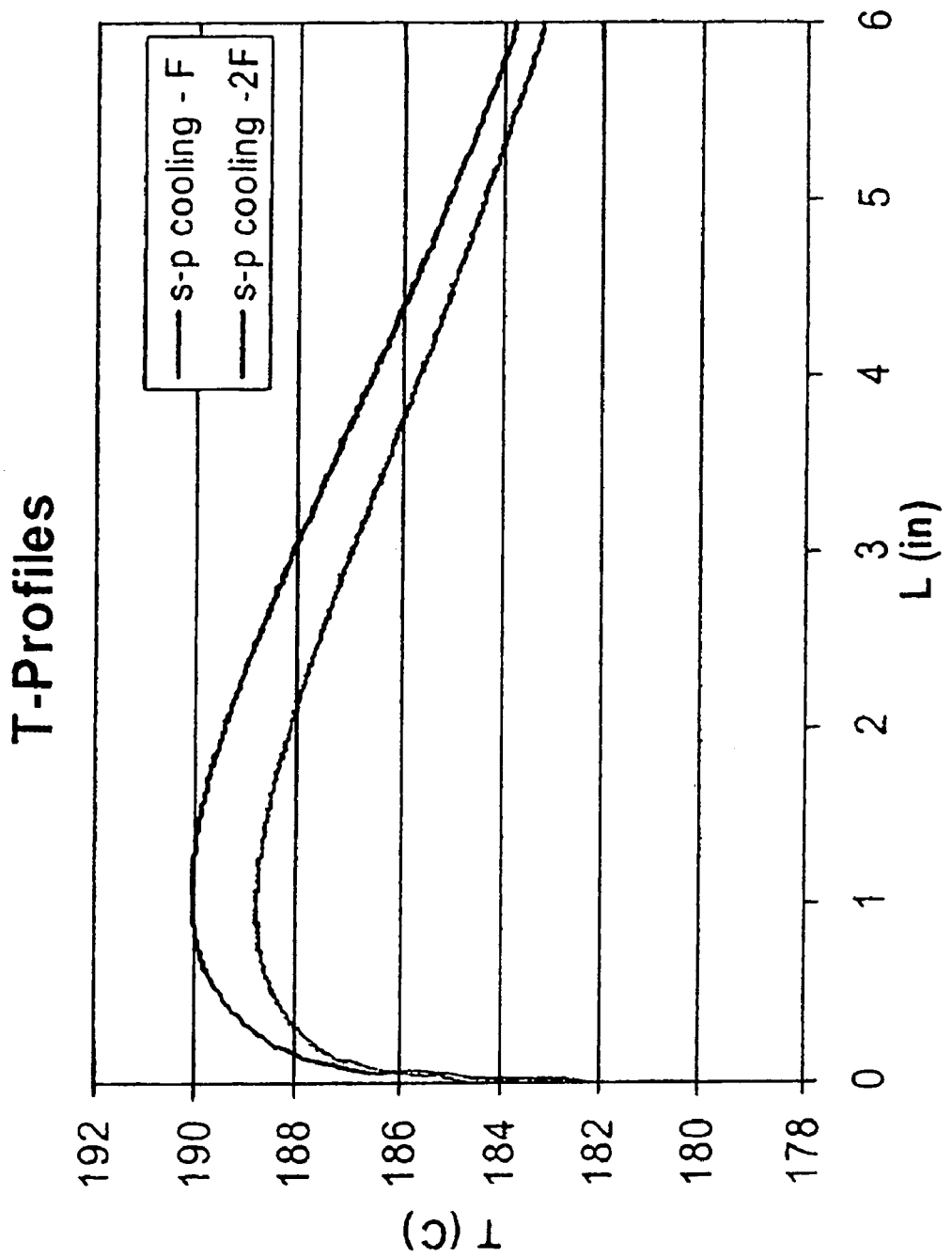

In conventional shell and tube reactors for VAM production, partial boiling of water on the shell side of the reactor is applied to remove the reaction heat. The results in FIG. 5a and FIG. 5b show that under certain operating conditions single phase convective heat transfer is sufficient to remove the reaction heat in a micro configuration. The reason is the available heat transfer surface area per unit reactor volume is much greater in micro-channel reactors than that in a conventional packed-bed reactor. If single phase convective heat transfer and surface area are sufficient to remove the reaction heat, several parameters should be used to optimize the heat removal in the heat exchange channels. The cooling flow rate can be increased to enhance the heat removal capability. The cooling channel gap is another parameter for design toward the desired heat removal capability. Decreasing the hydraulic diameter of the channel helps increase the convective heat transfer coefficient.

While co-current process and coolant stream flow is shown in these examples, cross-flow and countercurrent flow are also options.

In preferred embodiments, the inventive processes may also be characterized by per pass conversion of reactants and per pass selectivities to products. By "per pass" it is meant on a single traverse of a reaction channel (or in some embodiments through a reaction zone) without recycling. Of course the inventive methods can (and often will) be operated with a recycle step; however, a unique and unexpected aspect of invention is its high conversions coupled with excellent product selectivity that are obtained without a recycle step. The invention can be characterized by selected conversions and/or selectivities either individually or in any combination. Per pass conversion of dioxygen (also called "oxygen") is preferably at least 30%, more preferably 60%, still more preferably at least 80%, and yet more preferably at least 90%; in some embodiments 20-60%, in some embodiments 55-95%, and in some embodiments 50-75%. Per pass conversion of ethylene is preferably at least 20%, more preferably at least 30%, and in some embodiments about 25 to about 35%.

Selectivity to carbon dioxide is preferably less than 15% (based on how much of the ethylene is converted to carbon dioxide), more preferably less than 10%, and in some embodiments about 5 to 10%. The conversion and selectivity properties of the invention can also be derived from the data presented in the Examples section below.

Convective Boiling Cooling

Figure 6:
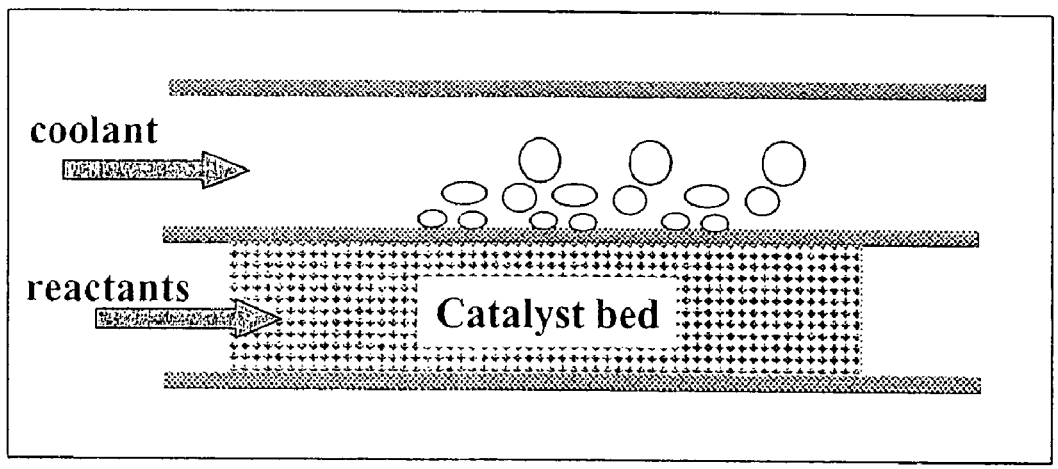
FIG. 6 schematically illustrates a cross-section of a reactor with adjacent partial boiling heat exchange.

Partial boiling heat transfer can be applied to vinyl acetate monomer (VAM) production in micro-channels. A calculated example is based on microchannels made with a combination of plates having cross-sectional dimension 0.020 inch thickness×0.5 inch width×3 inch length. The gap on the reaction side is 0.04 inch and on the coolant side is 0.04 inch. On the reaction side, a mixture of ethylene (C2H4), acid gas (CH3COOH) and oxygen (O₂) are fed at temperature 160° C. and pressure 8 atm. The micro-channel is packed with micro-pellet catalyst with the void fraction around 0.4. A schematic cross-sectional illustration of a reactor with adjacent partial boiling heat exchange is shown in FIG. 6.

The VAM producing reaction release heat into the packed bed and then the heat conducts through the channel walls to the surface on the coolant side, where the coolant vaporizes. The coolant used in this calculated example is water. At the beginning of the catalyst bed, the reactants are at the highest concentration level and the reaction rate is at the maximum. This leads to the asymmetrical temperature profile along the catalyst bed. Accordingly, the heat flux profile on the channel wall has the temperature peak near the inlet of the reactor.

Figure 7:
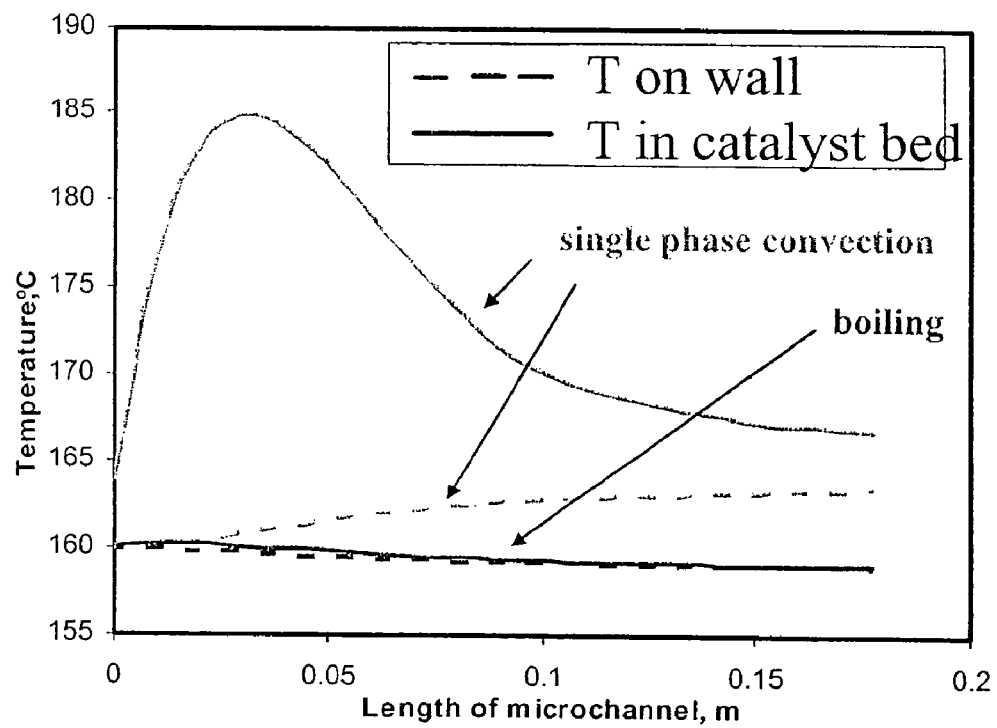
FIG. 7 shows calculated temperature profiles along the reactor length using different heat removal schemes. (mass flow rate on the process side is 146.2 Kg/m2 s, T$_{in}$=160° C.).

A temperature hot spot near the beginning of the catalyst bed is detrimental to the selectivity of the desired product—VAM and the product yield. Also, the catalyst lift time will be shortened due to the high temperature. It is desirable to operate the VAM reactor at the iso-thermal condition, or temperature variation along the reaction path within a tight range. In FIG. 7, temperature profiles along the reactor length using various heat removal schemes are compared. It shows that the temperature variation along the reactor length is much tighter when partial boiling is applied to remove the heat. Another advantage of applying partial boiling heat removal is that highly active catalyst can be used to give temperature profiles without large spikes.

Figure 8:
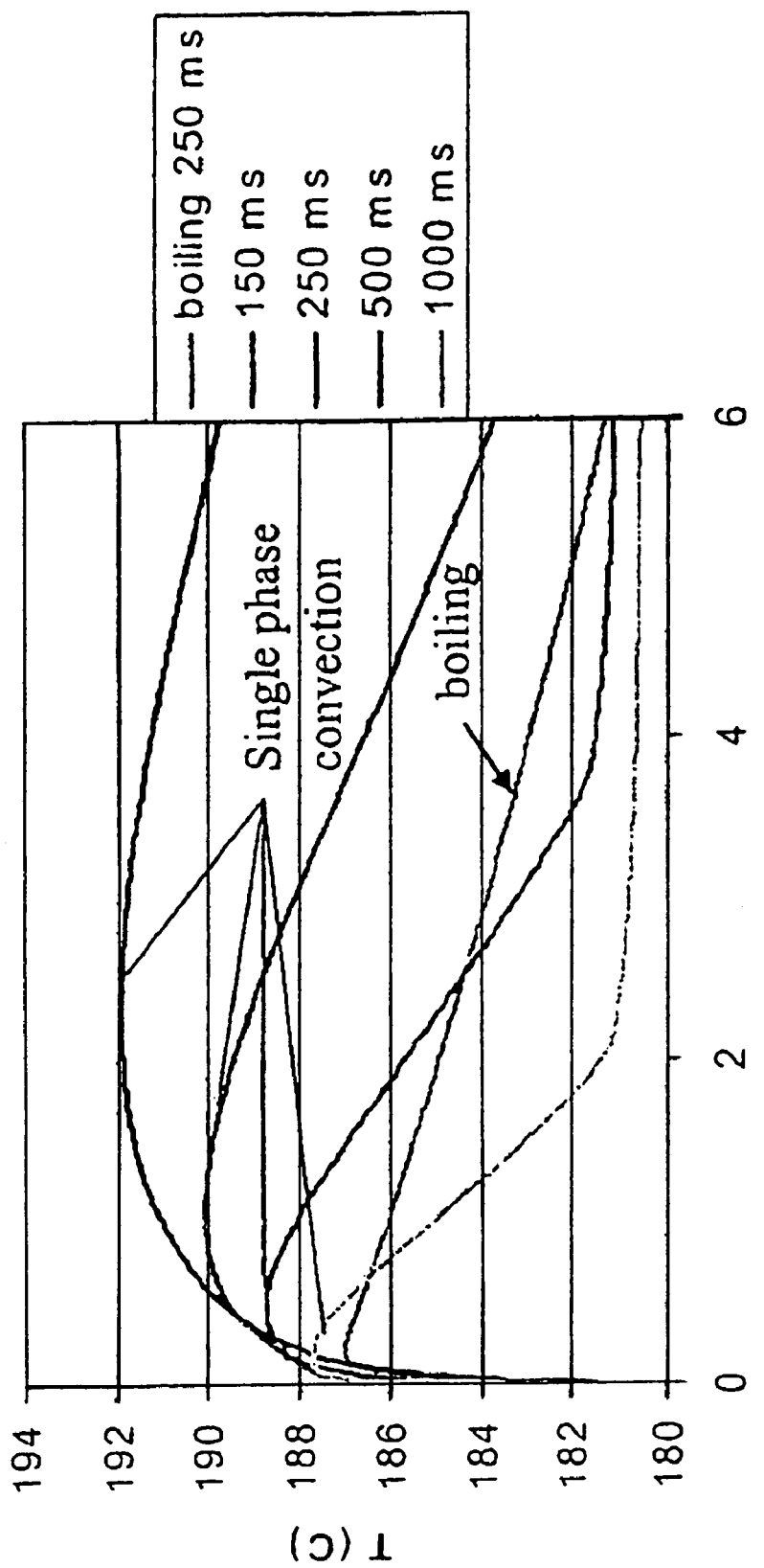
FIG. 8 shows temperature profiles along the centerline of the catalyst bed calculated under four contact time levels with single phase heat convection as the heat removal method. Partial boiling heat removal at 250 ms is also illustrated. T$_{in}$ (process)=180° C.; T$_{in}$ (cooling)=180° C.; V (cooling)=0.3 m/s.

FIG. 8 shows the temperature profiles along the centerline of the catalyst bed calculated under four contact time levels with single phase heat convection as the heat removal method. The gap size of the coolant channel is 0.04 inch. The wall thickness is 0.02 inch and the channel gap on the process side is 0.04 inch also. The coolant flow stream has the average velocity of 0.3 m/s. Under lower contact time, or larger throughput, the temperature rise in the catalyst bed is larger. At 250 ms contact time on the process side, if partial boiling is the choice of heat removal method, the temperature rise in the catalyst bed is less than 10° C.

As one alternative to partial boiling in a cooling channel, staging of reactants, preferably combined with single phase heat exchange, can be an effective technique to avoid hot spots and effectively manage temperature.

Micro-to-Macro Manifold Options

In some embodiments, the invention requires distributing at least one reactant from one channel into a second adjoining channel where a reaction is taking place. As it is desirable to keep the adjacent streams separate until the point(s) of mixing, the distribution of the fluids from macro scale fluid channels to the unit's microchannels should be designed to achieve the desired flow distribution.

It is possible for one reactant stream to use a large macro scale manifold to connect a relatively larger stream to relatively smaller, multiple, parallel microchannels. The direction of an inlet flow in a macro scale manifold can be aligned parallel, perpendicular or some intermediate angle with regard to the direction of the connecting channels (connecting channels may connect a header to a footer). Typically, one or more reactant streams uses a macro-to-micro (M2M) manifold for distribution within a microchannel unit.

Quality Index factor "$Q_1$" is a measure of how effective a manifold is in distributing flow. It is the ratio of the difference between the maximum and minimum rate of connecting channel flow divided by the maximum rate. For systems of connecting channels with constant channel dimensions it is often desired to achieve equal mass flow rate per channel. The equation for this case is shown below, and is defined as $Q_1$.

$$Q_1 = \frac{m_{max} - m_{min}}{m_{max}} \times 100\%$$

where
$m_{max}$[kg/sec]=maximum connecting channel mass flow rate
$m_{max}$[kg/sec]=minimum connecting channel mass flow rate For cases when there are varying connecting channel dimensions it is often desired that the residence time, contact time, velocity or mass flux rate have minimal variation from channel to channel such that the required duty of the unit operation is attained. For those cases we define a quality index factor $Q_2$:

$$Q_2 = \frac{G_{max} - G_{min}}{G_{max}} \times 100\%,$$

where G is the mass flux rate. For cases when all the connecting channels have the same cross sectional area, the equation for $Q_2$ simplifies to $Q_1$. The quality index factor gives the range of connecting channel flow rates, with 0% being perfect distribution, 100% showing stagnation (no flow) in at least one channel, and values of over 100% indicating backflow (flow in reverse of the desired flow direction) in at least one channel. In this invention, $Q_1$ and $Q_2$ are defined based on the channels that comprise 95% of the net flow through the connecting channels, the lowest flow channels are not counted if the flow through those channels is not needed to account for 95% of the net flow through the connecting channels. By selection of appropriate M2M designs for microchannel reactors, quality index factors for reactant flows can be below 20%. See Fitzgerald et al., U.S. patent application Ser. No. 10/695,400, now U.S. Pat. No., incorporated herein by reference.

EXAMPLES

1. Reactor Design

A device was designed that included an internal mixing zone and facility to monitor the reactor wall temperature at 10 different locations. The device was also fitted with means for introducing a heat transfer fluid along the length of the reaction zone in a parallel channel.

The reactors were constructed with rectangular catalyst zones of 1.5 inches long by 0.5 inches wide by 0.04 inches tall and 1.5 inches long by 0.5 inches wide by 0.08 inches tall (volumes 0.492 and 0.983 cc), referred to as a "40-gap" and "80-gap" reactor, respectively. Typically 0.336 g of catalyst was loaded into the 40-gap reactor. Cooling was provided by circulating mineral oil in a countercurrent stream on either side of the catalyst zone.

Figure 9:
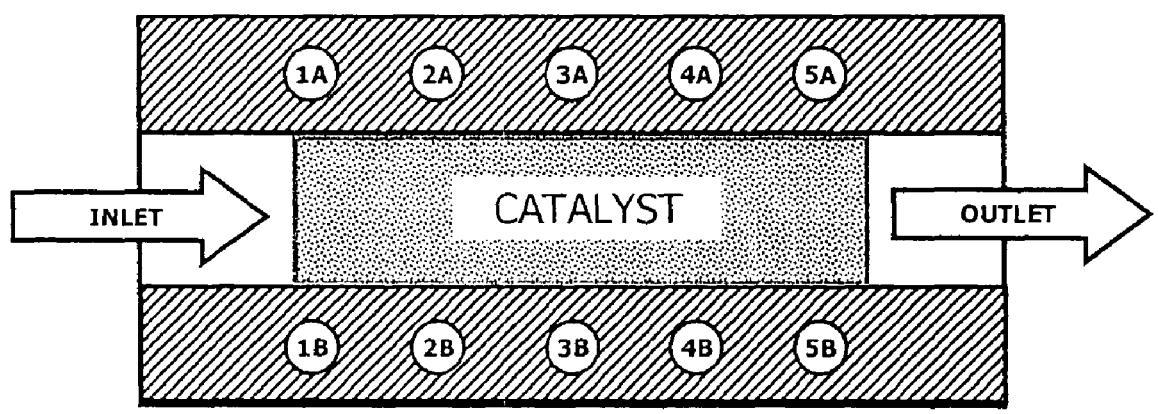
FIG. 9 shows thermocouple placement in the test reactors.

The reactors can be run under nearly isothermal conditions with high heat generation and removal. Typical temperature profiles of the wall along the catalyst bed (points 1A through 5A in FIG. 9) show temperature gradients of 1° C. or less.

2. Experimental

Installation/Startup

The catalyst test system consists of vaporizer/preheater to preheat the reactants, a reactor temperature controlled by a recirculating oil bath, a microchannel heat exchanger to cool the products and a dual chilled vapor liquid separator system.

The reactor was supported in a vertical position, and was packed with foam and quartz wool to hold the catalyst in place, and enough catalyst to fill 1.0 inch of reactor length. Upstream of the catalyst a small portion of the catalyst support impregnated with potassium acetate was packed into the channel.

Catalyst Preparation

Two catalysts were employed in conducting the tests to validate the invention. Catalysts 1 and 2 were prepared by crushing and sieving commercially available silica alumina particles (Catalyst 1) or zirconia (Catalyst 2) to give particles in the range of 80 to 140 microns The Pd (43.2 g/l of catalyst in the form of $Pd(NH_3)_4(OH)_2$ was added as an aqueous solution to the support using the incipient wetness method, the Pd-containing support was dried at 110° C. for 5 h and then calcined in air at 350° C. for 2 h. Sufficient $KAuO_2$ solution was added to give an Au loading of 28.0 g/l of catalyst is dried at 110 C for 5 h and then reduced at 150° C. under 5% $C_2H_4$ for 4 h (other reducing gases such as 1% $C_2H_4$ or 4% $H_2$ may be used). KOAc (40 g/l) was added to the reduced catalyst and then the catalyst was dried at 100° C. for 5 h. While these catalysts were prepared as "all through-out" catalysts, the concentrations of metals are typical of that found in the outer, catalytically active layer of eggshell catalysts. Since the size of the particles is of the same order as the shell thickness in an eggshell catalyst, Catalysts 1 and 2 can be expected to give similar performance to that would be obtained on catalysts prepared on other, non-powdered support structures.

The reactor was charged with 1.2 cc of the catalyst and a charge of 0.3 cc of silica impregnated with 40 g per liter of KOAc in the region immediately before the catalyst. The catalyst is held in place by a small piece of FeCrAlY foam and quartz wool.

Testing Procedure

All inlet and outlet stream temperatures were measured using type K thermocouples placed in the connecting tubes to the reactor system approximately 2 to 5 cm from the inlet or outlet of the reactor. Pressure transducers were added to each of the inlet and outlet streams at similar locations. Thermocouples were also installed in thermocouple ports on the outer surface of the reactor system along the length of the mixer and reactor sections.

The reactant feed Brooks 5850e series mass flow controllers, HPLC single piston acetic acid pump, NoShok pressure transducers model 1001501127 and 1003001127, Omega latching relay controllers model CNI 1653-C24, Swagelok variable pressure relief valves, thermal conductivity detector (TCD) gas chromatograph for gas analysis, flame ionization detector (FID) gas chromatograph for liquid analysis, etc were calibrated and verified for proper operation. Flowrates were calibrated against a primary standard calibrator, the Dry-Cal DC-2M Primary Flow Calibrator, which was calibrated and certified by BIOS International. Pressure transducers were calibrated using a Fluke pressure calibrator model 7181006 with a Fluke 700P07 or 700P06 pressure module which were calibrated and certified by Fluke. The TCD gas chromatograph was calibrated against calibration gases blended and certified by Praxair Distribution Inc. The FID gas chromatograph was calibrated with an in-house mixed solution which was measured by volume, and double checked by mass.

The reactor system was pressure tested by applying a static pressure of ~150 psig using nitrogen fluid. If the leak rate did not exceed 0.5 psig in 15 minutes, then the reactor system was considered ready for operation.

Flowing nitrogen, the system was pressurized to the run plan operating pressure at ~5-8 psig/min. The reactor was then heated at 5° C./min to the run plan operating temperature by the flow of hot oil, and the inlet and outlet lines of the catalyst test system are heating using electrical heating tape to a minimum of 140° C. to prevent acetic acid condensation. The gaseous reactants, typically ethylene and nitrogen, were preheated concurrently with the vaporization of acetic acid to 170-200° C. The vaporizer/preheater was a ⅜" 316 stainless steel tube wrapped in a 4 foot, 312W electrical resistance heat tape. Control of the heat tape was achieved using an Omega controller. The oxygen or air reactant was not preheated prior to entrance into the reactor. The main system knockout drum was then set and operated at 8° C., while the final knockout drum was operated at −10.5° C. Then the reactant flows were initiated. Ethylene was slowly turned up to the run plan flowrate while the process side nitrogen was adjusted to the tracer flowrate. Then acetic acid was initiated to the run plan flowrate. After the system was stable at the proper temperature and pressure, oxygen was slowly turned on while the oxygen side nitrogen was slowly turned off.

In the first tests the products collected in the cold traps were analyzed by GC. Vinyl acetate monomer was identified as the primary product in the liquid in an amount appropriate for the temperature of the trap and vapor pressure of vinyl acetate that was vented along with the gaseous effluents. Carbon balances between 95 and 105% were obtained by complete analysis of the liquid and gaseous products. In further experiments the yield of vinyl acetate was obtained by subtracting the amount of $CO_2$ measured in the gaseous products from the amount of ethylene converted, assuming that one molecule of vinyl acetate was formed from every ethylene converted to vinyl acetate and that two molecules of $CO_2$ were formed from every molecule of ethylene converted to $CO_2$. Oxygen conversion was measured by subtracting the amount of oxygen measured in the products from the oxygen fed to the reactor.

3. Results

A series of experiments were conducted to evaluate the performance of catalysts in reactors to measure performance of the system under a variety of reaction conditions (temperature, partial pressures of feeds, contact time, etc.). The results are provided in Tables 1 and 2 and a short summary of some of the results is discussed below. The data are provided in the tables and discussion are intended to be illustrative of the kinds of results obtained from the present invention, but not all results are presented. In view of the results and descriptions provided here, workers skilled in the art can understand the benefits of the invention and process conditions that would provide beneficial results.

Figure 10:
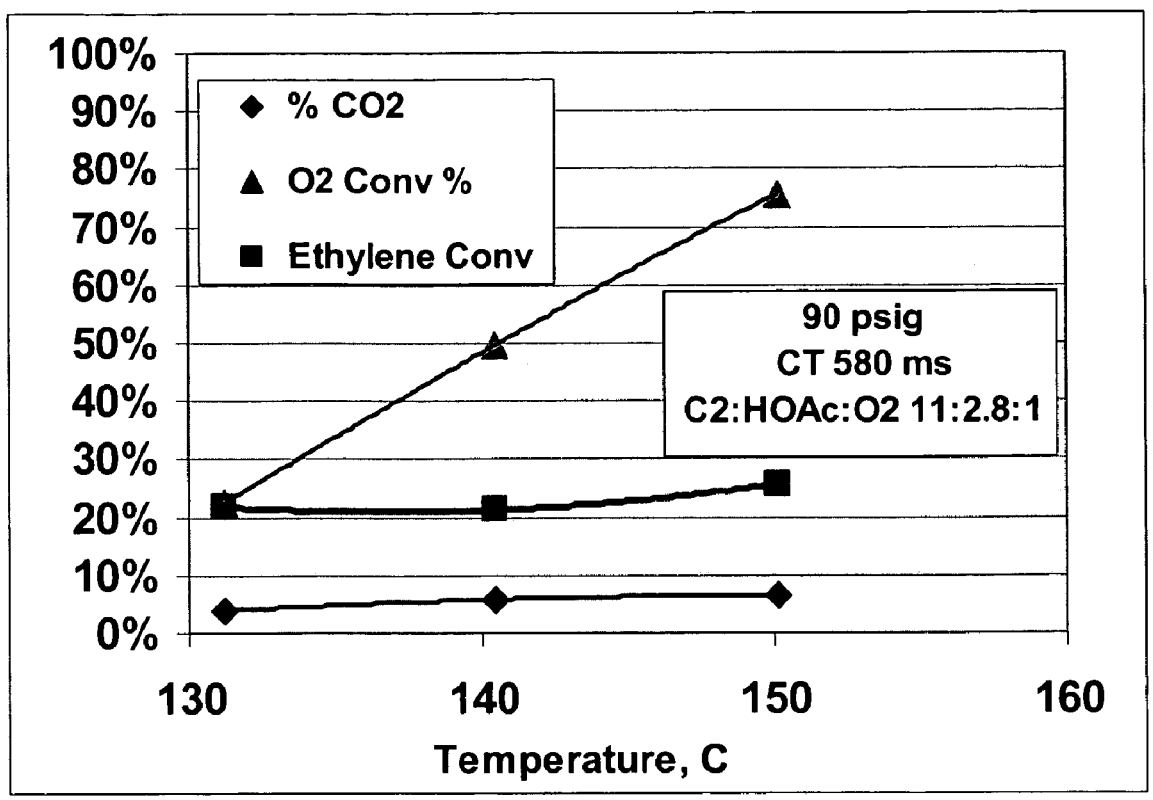
FIG. 10 shows the effect of temperature on the performance of Catalyst 1 at 90 psig and 580 ms contact time with a high C2:Acid:O2 ratio.

In this series of experiments air was the source of oxygen and a large excess of ethylene was used (ethylene:HOAc:oxygen 11:2.8:1). The pressure was 90 psig and the contact time was 580 ms. At 150 C the oxygen conversion reached 76% and the $CO_2$ selectivity was 13%. The data are summarized in FIG. 10. As can be seen from the figure, it was possible to achieve very high oxygen conversion while maintaining excellent selectivity to desired products (below 10% selectivity to carbon dioxide). Ethylene conversion was low in these experiments due to the large excess of ethylene (ethylene:dioxygen=11:1).

Figure 11:
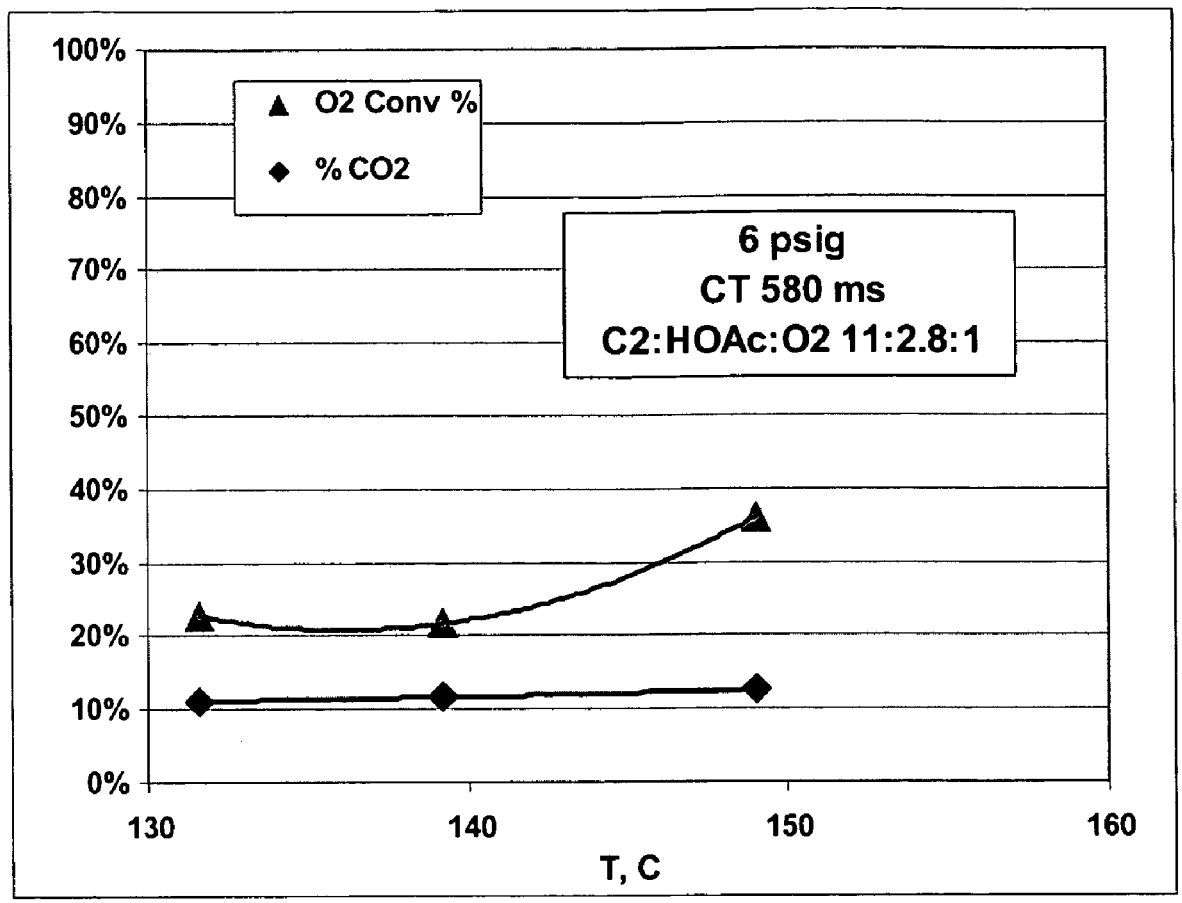
FIG. 11 shows the effect of temperature on the performance of Catalyst 1 at low pressure (6 psig) and long contact time (580 ms). O$_2$ was fed as air.

A similar set of experiments was conducted at a much lower pressure, 6 psig, with the same catalyst. FIG. 11 presents the results of these tests. The conversion of oxygen and the selectivity to $CO_2$ were inferior to the high pressure tests, with a maximum $O_2$ conversion of only 36% and the CO2 selectivity always above 20%.

Figure 12:
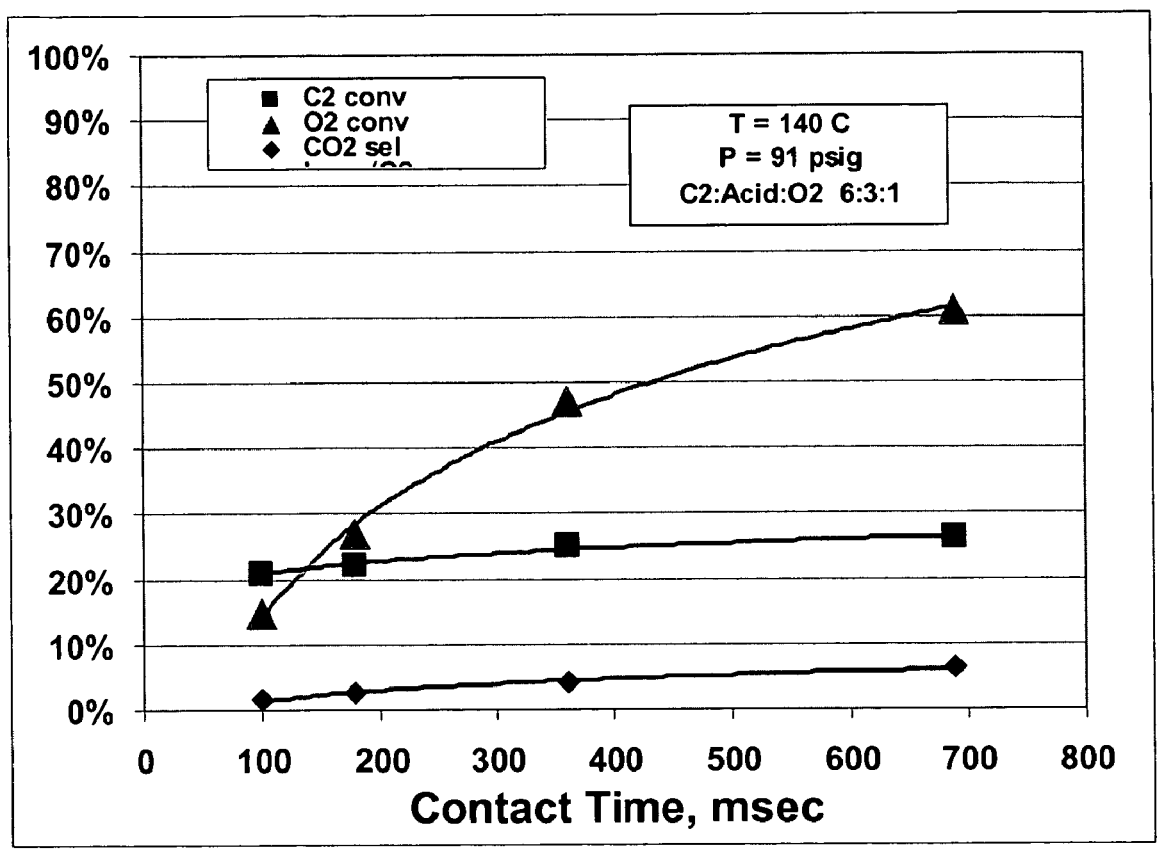
FIG. 12 shows the performance of Catalyst 1 as a function of contact time (1/space velocity) at 140 C and 95 psig with a 6:3:1 C2:Acid:O2 feed. O$_2$ was fed as air.
Figure 13:
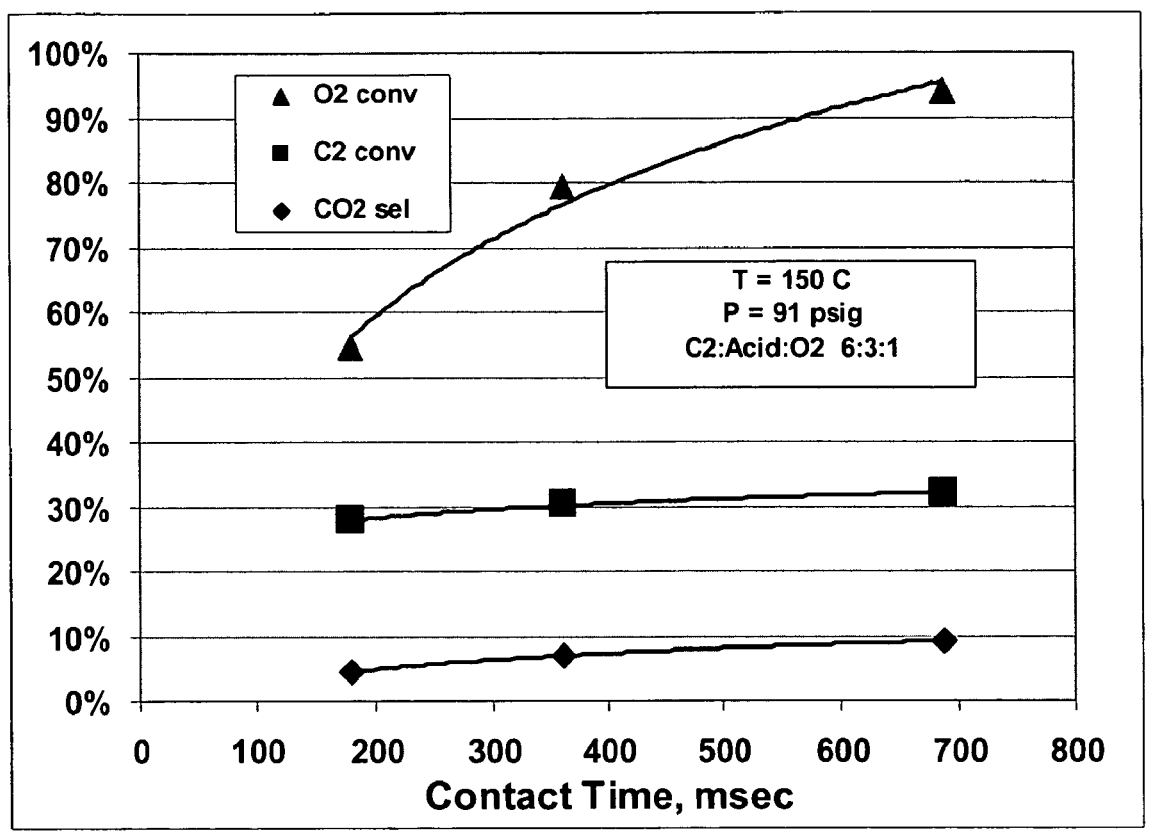
FIG. 13 shows the performance of Catalyst 1 as a function of contact time (1/space velocity) at 150° C. and 91 psig with a 6:3:1 C2:Acid:O2 feed. O$_2$ was fed as air.

FIGS. 12 and 13 present results of the dependence of catalyst performance on contact time for Catalyst 1. The feed in these experiments was a 6:3:1 mixture of ethylene, acetic acid and oxygen, with the oxygen fed as air. At 140° C. and 91 psig the maximum oxygen conversion was 61% with a 12.5% $CO_2$ selectivity when the contact time was 689 ms. At faster flow rates (lower contact times) the oxygen conversion was lower and the $CO_2$ selectivity was lower.

When the contact time study was repeated at 150° C. the oxygen conversions were higher, ranging from 55 to 94%, and the $CO_2$ selectivities ranged from 9 to 18% as the contact time was increased from 181 to 689 ms. The data are presented in FIG. 13.

Figure 14:
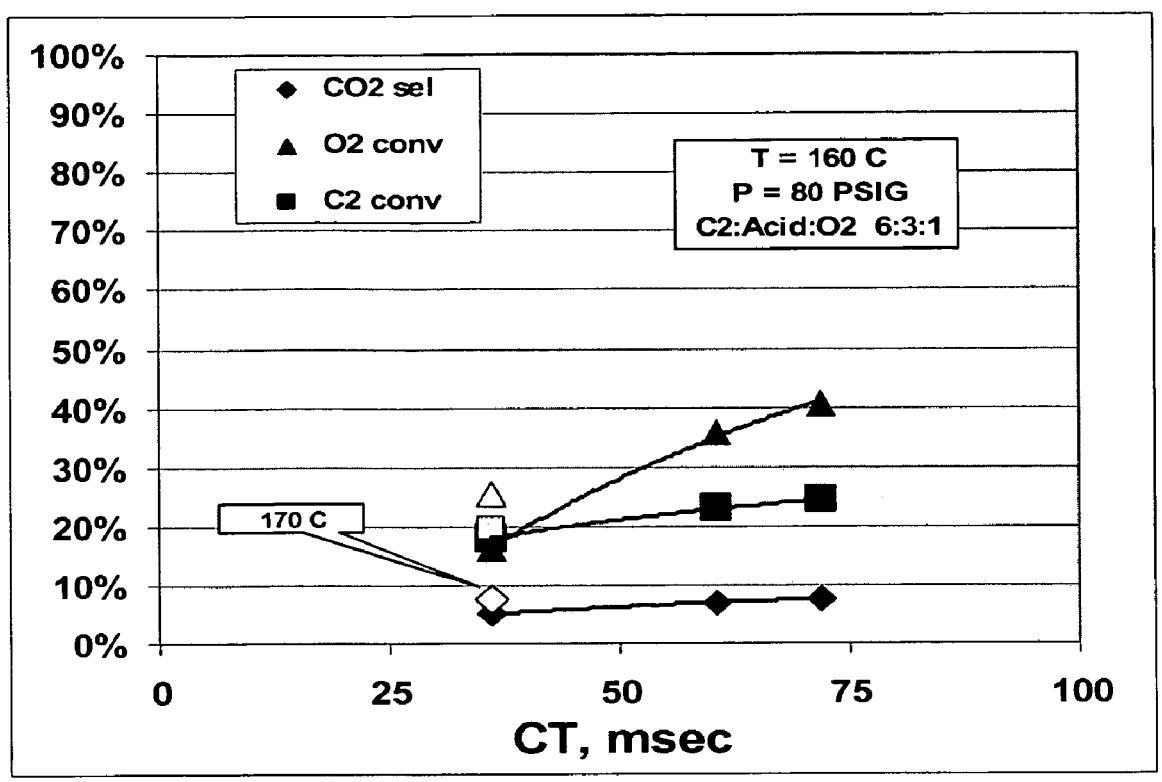
FIG. 14 shows the effect of contact time on catalyst performance at fast flow rates.

Still faster flow rates were investigated using the same catalyst and feed ratios as in the previous experiments, and a set temperature of 160° C. When the contact times were varied from 36 to 72 ms the oxygen conversions ranged from 16 to 41% and the $CO_2$ selectivities from 5.1 to 7.7%. The 36 ms experiment was repeated at 170° C., and the oxygen conversion increased from 16 to 25% while the $CO_2$ selectivity increased to from 5.1 to 7.6%. These data are summarized in FIG. 14.

Figure 15:
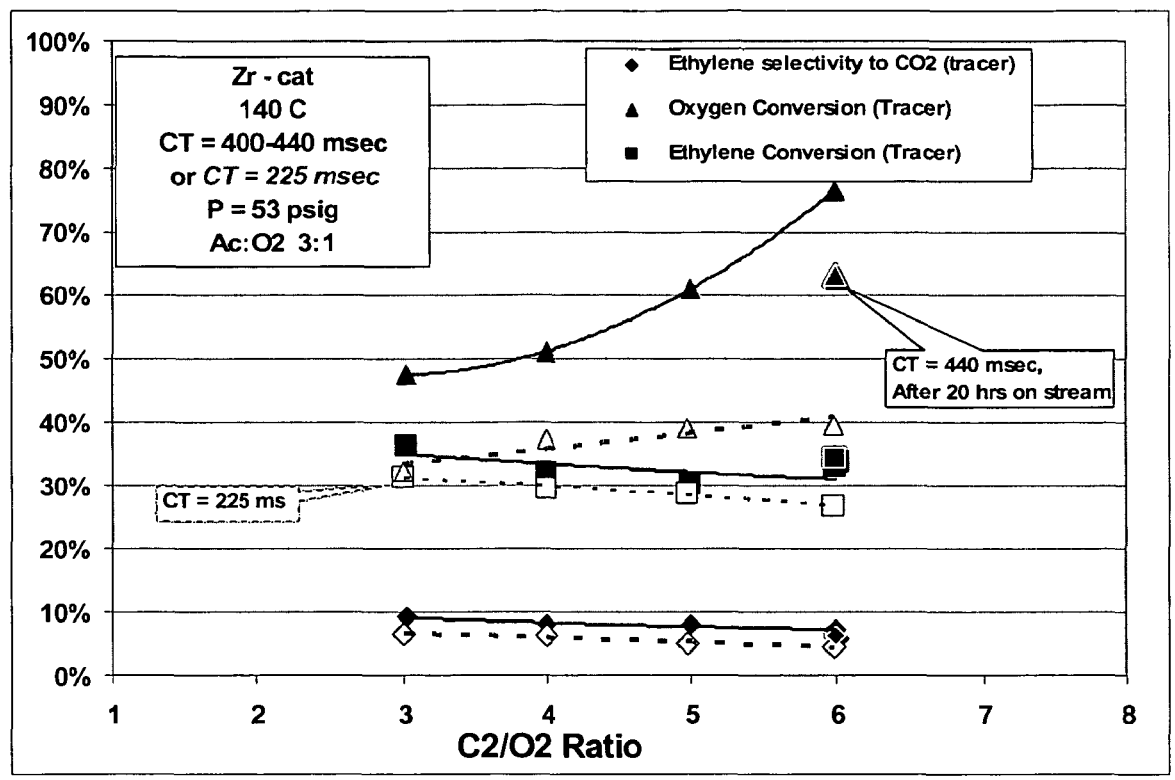
FIG. 15 shows the effect of varying C2/O2 ratio on performance of Catalyst 2 at two different contact times.

A $ZrO_2$ supported catalyst (Catalyst 2) was tested for comparison to the $SiO_2$ supported catalyst. A 1.261 g sample of catalyst was charged to an "80-gap" reactor. FIG. 15 summarizes the results of the performance of this catalyst as a function of the ethylene/oxygen ratio at two different contact times. The oxygen conversion reached as much as 77% at the longer contact time (440 ms) with a 6/3/1 ethylene/acid/oxygen feed. Under these conditions the $CO_2$ selectivity was only 7.2%.

The data in FIGS. 10-15 show that the increase in oxygen conversion is more rapid (larger slope) than the increase in selectivity to carbon dioxide when utilizing the system according to the invention. Taken together, the results demonstrate superior results over a wide range of reaction conditions. This result is surprising in light of the prior art. For example, U.S. Pat. No. 6,022,823 described experiments conducted in a 1 inch outer diameter tubular reactor containing 30 ml of catalyst with a bed height of 3 inches. This configuration has a high heat transfer surface area to reaction zone volume of 1.78 $cm^{-1}$. Data provided for the reactions in that reactor show that, while it is possible to achieve high levels of oxygen conversion, the selectivity to VA is low. Further, their data shows that the selectivity to VA decreases dramatically as the oxygen conversion is increased.

Tables 1 and 2 provide further examples of results obtained that demonstrate the effectiveness of the invention in achieving high conversion of oxygen, ethylene and/or acetic acid while simultaneously achieving high selectivity to VA, here measured as low selectivity to CO2.

TABLE 1

|  |  | Catalyst 2 | Catalyst 2 | Catalyst 2 |
|---|---|---|---|---|
| ethylene | sccm | 21.2 | 21.2 | 21.2 |
| acetic acid | sccm | 11.8 | 11.8 | 11.8 |

TABLE 1-continued

|  |  | Catalyst 2 | Catalyst 2 | Catalyst 2 |
|---|---|---|---|---|
| oxygen | sccm | 3.5 | 3.5 | 3.5 |
| nitrogen tracer | sccm | 3.9 | 3.9 | 3.9 |
| Inlet Pressure | (psig) | 55.92 | 52.6 | 53.2 |
| Pressure Drop | (psi) | 55.7 | 52.2 | 53.0 |
| Contact Time | (ms) | 1487 | 1487 | 1487 |
| Ethylene Conversion | (%) | 16.8% | 14.1% | 5.8% |
| Ethylene selectivity to CO2 | (%) | 2.6% | 11.3% | 17.0% |
| Oxygen Conversion | (%) | 93.3% | 83.7% | 97.4% |
| Oxygen selectivity to CO2 | (%) | 2.8% | 11.6% | 6.1% |
| O2 conversion to CO2 | (%) | 2.7% | 9.8% | 6.1% |
| Bed avg temperature | (C.) | 128 | 138 | 150 |
| C2H4:O2 | (mol/mol) | 6.06 | 6.06 | 6.06 |
| CH3COOH:O2 | (mol/mol) | 3.36 | 3.36 | 3.36 |
| HOAc Conversion | (%) | 29.5% | 22.6% | 8.7% |

TABLE 2

| Catalyst | Contact Time (ms) | $C_2H_4:O_2$ (mol/mol) | $CH_3COOH:O_2$ (mol/mol) | Bed avg temp (C.) | Nitrogen Tracer ($N_2$) (sccm) |
|---|---|---|---|---|---|
| 1 | 425 | 5.21 | 3.34 | 150 | 22.23 |
| 1 | 346 | 3.81 | 2.46 | 150 | 24.20 |
| 1 | 346 | 3.81 | 2.46 | 150 | 24.20 |
| 1 | 346 | 3.81 | 2.46 | 150 | 24.20 |
| 1 | 279 | 7.13 | 4.54 | 164 | 32.50 |
| 1 | 346 | 3.81 | 2.46 | 150 | 24.20 |
| 1 | 346 | 3.81 | 2.46 | 150 | 24.20 |
| 1 | 346 | 3.81 | 2.46 | 150 | 24.20 |
| 1 | 425 | 5.21 | 3.34 | 151 | 22.23 |
| 1 | 425 | 5.21 | 3.34 | 151 | 22.23 |
| 1 | 425 | 5.21 | 3.34 | 151 | 22.23 |
| 1 | 425 | 5.21 | 3.34 | 151 | 22.23 |
| 1 | 425 | 5.21 | 3.34 | 151 | 22.23 |
| 1 | 425 | 5.21 | 3.34 | 151 | 22.23 |
| 2 | 444 | 6.00 | 3.32 | 140 | 6.6 |
| 2 | 409 | 5.00 | 3.27 | 140 | 6.6 |

| Oxygen Conversion (%) | Ethylene Conversion (%) | HOAc Conversion (%) | Ethylene selectivity to CO2 (%) | Oxygen selectivity to CO2 (%) |
|---|---|---|---|---|
| 79.3% | 31.7% | 75.2% | 8.1% | 33.7% |
| 79.0% | 37.8% | 55.1% | 5.8% | 21.2% |
| 79.3% | 32.6% | 47.0% | 7.0% | 21.9% |
| 76.8% | 35.9% | 52.5% | 5.6% | 20.1% |
| 88.2% | 25.0% | 61.1% | 5.6% | 22.8% |
| 80.7% | 38.2% | 55.7% | 5.8% | 21.0% |
| 80.1% | 37.9% | 55.2% | 6.0% | 21.5% |
| 80.3% | 34.2% | 49.7% | 6.2% | 20.2% |
| 82.4% | 31.8% | 76.0% | 7.5% | 30.2% |
| 82.6% | 32.0% | 76.2% | 7.8% | 31.5% |
| 82.4% | 32.1% | 76.4% | 7.8% | 31.7% |
| 82.4% | 30.3% | 71.9% | 8.1% | 31.2% |
| 81.2% | 31.7% | 75.6% | 7.7% | 31.4% |
| 82.0% | 32.0% | 76.1% | 7.9% | 32.0% |
| 76.6% | 33.0% | 44.7% | 7.2% | 18.7% |
| 61.0% | 30.2% | 57.4% | 7.9% | 19.6% |

What is claimed:

1. Apparatus for the production of VAM, comprising:
a continuous reaction channel comprising at least 2 catalyst-free mixing zones alternating with at least 2 catalyst-containing reaction zones; and
a cooling channel adjacent to the reaction channel.

2. The apparatus of claim 1 wherein the catalyst in the at least 2 catalyst-containing reaction zones comprises more than 10 wt % Pd.

3. The apparatus of claim 1 wherein the continuous reaction channel comprises a microchannel having at least one dimension of 2 mm or less.

4. The apparatus of claim 3 wherein the at least 2 catalyst-containing reaction zones are microchannel reaction zones having at least one dimension of 2 mm or less.

5. The apparatus of claim 3 made by laminating interleaved plates comprising plates designed for reaction channels interleaved with plates designed for heat exchange.

6. The apparatus of claim 1 wherein the catalyst is a thin layer or rim-type catalyst, and wherein the catalyst comprises more than 10 wt % Pd.

7. A system comprising the apparatus of claim 1 wherein the at least 2 catalyst-free mixing zones comprise dioxygen, ethylene and acetic acid; and wherein the cooling channel comprises a heat exchange fluid.

8. The apparatus of claim 1 comprising a plurality of the continuous reaction microchannels arranged in an array of microchannels.

9. The apparatus of claim 8 wherein the planar array of microchannels is in thermal contact with a plurality of adjacent heat exchange microchannels.

10. The apparatus of claim 1 wherein the reaction channel is cylindrical.

11. The apparatus of claim 1 wherein the at least 2 catalyst-containing reaction zones are adjacent to cooling channels; and further wherein the at least 2 catalyst-containing reaction zones have a ratio of heat transfer surface area to reaction zone volume of greater than 2.0 $cm^{-1}$.

12. The apparatus of claim 1 wherein at least 2 catalyst-containing reaction zones have a surface-to-volume ratio of at least 10 $cm^2$ of channel internal surface area per cubic centimeter of internal channel volume.

13. The apparatus of claim 1 wherein the reaction channel comprises plural porous sections disposed at least 2 catalyst-free mixing zones along the length of the reaction channel.

14. The apparatus of claim 13 wherein the reaction channel is a tube in a tubular reactor, and comprising a porous section on the periphery of the channel near a connection with a tube sheet.

15. The apparatus of claim 2 wherein the catalyst comprises a zirconia support.

16. The apparatus of claim 2 comprising at least 20 cc of solid catalyst.

* * * * *